: US011007125B2

(12) United States Patent
Ishizaki et al.

(10) Patent No.: US 11,007,125 B2
(45) Date of Patent: May 18, 2021

(54) TOOTH-SURFACE-MEMBRANE-FORMING POWDER CONTAINING SINTERED APATITE

(71) Applicant: KABUSHIKI KAISHA SANGI, Tokyo (JP)

(72) Inventors: Tsutomu Ishizaki, Tokyo (JP); Tadayoshi Arakawa, Tokyo (JP); Kazushi Ota, Tokyo (JP)

(73) Assignee: Kabushiki Kaisha Sangi, Tokyo (JP)

( * ) Notice: Subject to any disclaimer, the term of this patent is extended or adjusted under 35 U.S.C. 154(b) by 318 days.

(21) Appl. No.: 15/742,747

(22) PCT Filed: Jul. 12, 2016

(86) PCT No.: PCT/JP2016/003297
§ 371 (c)(1),
(2) Date: Jan. 8, 2018

(87) PCT Pub. No.: WO2017/010089
PCT Pub. Date: Jan. 19, 2017

(65) Prior Publication Data
US 2018/0250200 A1  Sep. 6, 2018

(30) Foreign Application Priority Data
Jul. 13, 2015 (JP) .............................. JP2015-139692

(51) Int. Cl.
*C09K 3/00* (2006.01)
*A61K 6/838* (2020.01)
(Continued)

(52) U.S. Cl.
CPC ............... *A61K 6/838* (2020.01); *A61K 6/17* (2020.01); *A61K 6/20* (2020.01); *A61K 6/78* (2020.01);
(Continued)

(58) Field of Classification Search
USPC ......................................................... 106/35
See application file for complete search history.

(56) References Cited

U.S. PATENT DOCUMENTS

| 4,847,163 A | 7/1989 | Shimamune et al. |
| 4,957,674 A | 9/1990 | Ichitsuka et al. |

(Continued)

FOREIGN PATENT DOCUMENTS

| JP | 64-86975 | 3/1989 |
| JP | H0339165 A | 2/1991 |

(Continued)

OTHER PUBLICATIONS

Sato et al., Creation of Hydroxyapatite film on Human Enamel Utilized Powder Jet Deposition, as supplied by applicants (Year: 2013).*

(Continued)

*Primary Examiner* — James E McDonough
(74) *Attorney, Agent, or Firm* — Occhiuti & Rohlicek LLP

(57) ABSTRACT

In order to provide a film-forming powder using hydroxyapatite which is a main component of teeth, or hydroxyapatite in which a color tone adjuster is blended, the powder being used in a jet-device for forming a film on a surface of a tooth by spraying the powder on the tooth, and being suitable for forming a film having a high hardness and extremely low solubility in acid in a short period of time, and suitable for forming a film of a powder conforming to the color tone of a tooth in a short period of time; a hydroxyapatite powder calcined in an inert gas atmosphere at 600 to 1350° C., a powder obtained by applying to the hydroxyapatite powder calcined at 600 to 1350° C. plasma irradiation, or plasma irradiation and mechanical energy, and additionally a film-forming powders obtained by blending (Continued)

color tone adjusters into these hydroxyapatite powders are produced.

19 Claims, 6 Drawing Sheets

(51) Int. Cl.
| | |
|---|---|
| A61K 6/17 | (2020.01) |
| A61K 6/20 | (2020.01) |
| A61K 6/78 | (2020.01) |
| B05B 1/30 | (2006.01) |
| B05D 1/12 | (2006.01) |
| C04B 35/626 | (2006.01) |
| C01B 25/32 | (2006.01) |

(52) U.S. Cl.
CPC ............ B05B 1/3006 (2013.01); B05D 1/12 (2013.01); C01B 25/327 (2013.01); C04B 35/6262 (2013.01); C04B 35/6268 (2013.01); C04B 35/62665 (2013.01); C04B 35/62675 (2013.01); B05D 2401/32 (2013.01); C01P 2004/61 (2013.01); C01P 2004/62 (2013.01)

(56) References Cited

U.S. PATENT DOCUMENTS

| | | | |
|---|---|---|---|
| 5,137,534 | A | 8/1992 | Sumita |
| 5,833,959 | A | 11/1998 | Atsumi et al. |
| 2004/0099998 | A1 | 5/2004 | Ishikawa et al. |
| 2006/0292088 | A1 | 12/2006 | Maitra et al. |
| 2010/0247589 | A1* | 9/2010 | Fahnestock .............. A61K 8/29 424/401 |
| 2010/0273129 | A1 | 10/2010 | Yu et al. |
| 2015/0250562 | A1 | 9/2015 | Urakabe et al. |
| 2016/0058528 | A1 | 3/2016 | Kim |
| 2016/0113736 | A1 | 4/2016 | Kuriyagawa et al. |
| 2016/0220452 | A1 | 8/2016 | Donnet |
| 2018/0200154 | A1 | 7/2018 | Ishizaki et al. |

FOREIGN PATENT DOCUMENTS

| | | |
|---|---|---|
| JP | H3-039165 A | 1/1993 |
| JP | 2001-178813 | 7/2001 |
| JP | 3340265 | 8/2002 |
| JP | 2005-029432 A | 2/2005 |
| JP | 2005-76113 | 3/2005 |
| JP | 3962061 | 5/2007 |
| JP | 3971877 | 6/2007 |
| JP | 2009-530005 | 8/2009 |
| JP | 4672112 | 1/2011 |
| JP | 5031398 | 7/2012 |
| JP | 2013-215240 | 10/2013 |
| JP | 2015-104429 | 6/2015 |
| KR | 20130009482 A * | 1/2013 |
| WO | 8102670 A1 | 10/1981 |
| WO | 2007/107729 | 9/2007 |
| WO | 2012173376 A2 | 12/2012 |
| WO | WO 2015/032758 | 3/2015 |

OTHER PUBLICATIONS

Akatsuka et al., Characteristics of hydroxyapatite film formed on human enamel with the powder jet deposition technique, as supplied by applicants. (Year: 2001).*

Farzadi, A. et al., Ceramics International, 40/4, pp. 6021-6029, May 2014.

Akatsuka et al., "Short Communication: Effect of hydroxyapatite film formed by powder jet deposition on dentin permeability." Eur J Oral Sci 2012; vol. 120, No. 6: pp. 558-562.

Akatsuka et al., "Characteristics of hydroxyapatite film formed on human enamel with the powder jet deposition technique." J Biomed Mater Res B Appl Biomater, 2011, vol. 98B, No. 2, pp. 210-218.

Akamatsu et al., "An Atmospheric Pressure, Low Temperature Plasma Jet for Laboratory Work." Research Bulletin of Kobe City College of Technology No. 50, 2012, 6 pages. English Abstract only.

Dental Tools and Materials Investigation and Research Committee, "Appropriate Values of Physical and Mechanical Properties that Dental Restorations are Expected to Have." Dental Materials and Instruments, 16 (6), pp. 555-562, 1997, Partial Translation, 9 pages.

Kitano et al., Let's Generate Atmospheric Pressure Plasma. J. Plasma Fusion Res. vol. 84, No. 1, pp. 19-28, 2008, Partial Translation, 11 pages.

Noji et al., "Characteristics of the hydroxyapatite film deposited on human enamel: deposition of a ceramic film by powder jet deposition technique." Int J Abrasive Technology, 2009, vol. 2, No. 1, pp. 83-96, 17 pages.

Notification of Transmittal of Translation of the International Preliminary Report on Patentability and International Preliminary Report on Patentability for International Application No. PCT/JP2016/003297 issued by The International Bureau of WIPO dated Jan. 25, 2018, 6 pages.

Notification of Transmittal of Translation of the International Preliminary Report on Patentability and International Preliminary Report on Patentability for International Application No. PCT/JP2016/003298 issued by The International Bureau of WIPO dated Jan. 25, 2018, 6 pages.

Sato et al., "Creation of Hydroxyapatite Film on Human Enamel Utilized Powder Jet Deposition." Transactions of the Japan Society of Mechanical Engineers (Series C), Dec. 25, 2013, vol. 79, No. 808, pp. 4634-4642.

Shiratori et al., "Research in Atmospheric Pressure Plasma—Research in Particle Accelerator for Science Education." Research Result Report of Nagano Prefecture School Science Education Encouragement Fund collaborating with Tokyo Institute of Technology, 2013, 12 pages. Partial Translation.

Rupf et al. "Killing of adherent oral microbes by a non-thermal atmospheric plasma jet." 2010. Journal of Medical Microbiology. vol. 59. pp. 206-212. (Year: 2010).

* cited by examiner

[Figure 1]
PLASMA GENERATOR
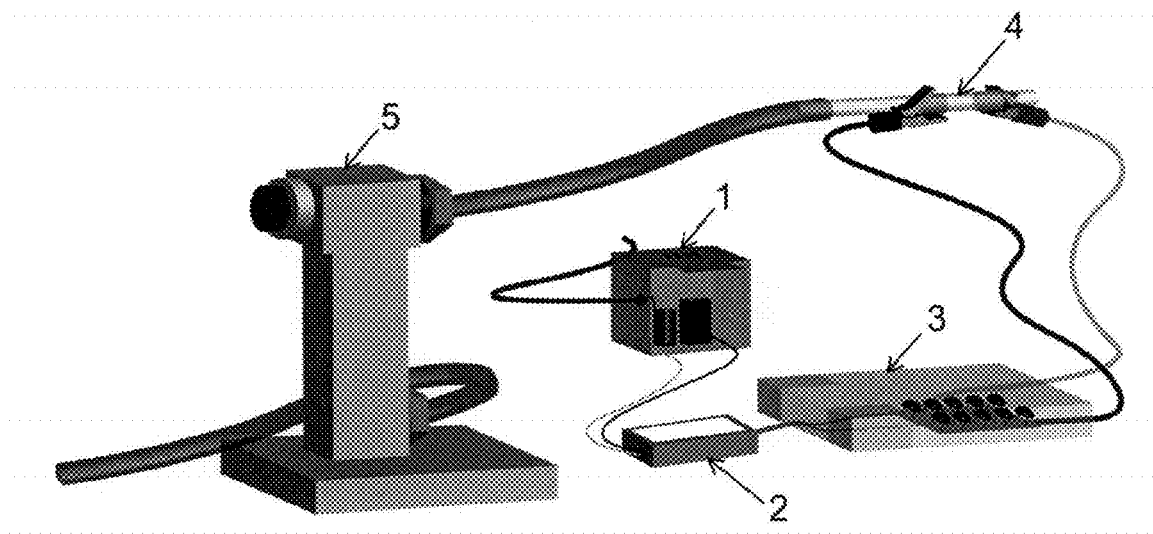
[Figure 2]
BOOSTER CIRCUIT (COCKCROFT-WALTON CIRCUIT)
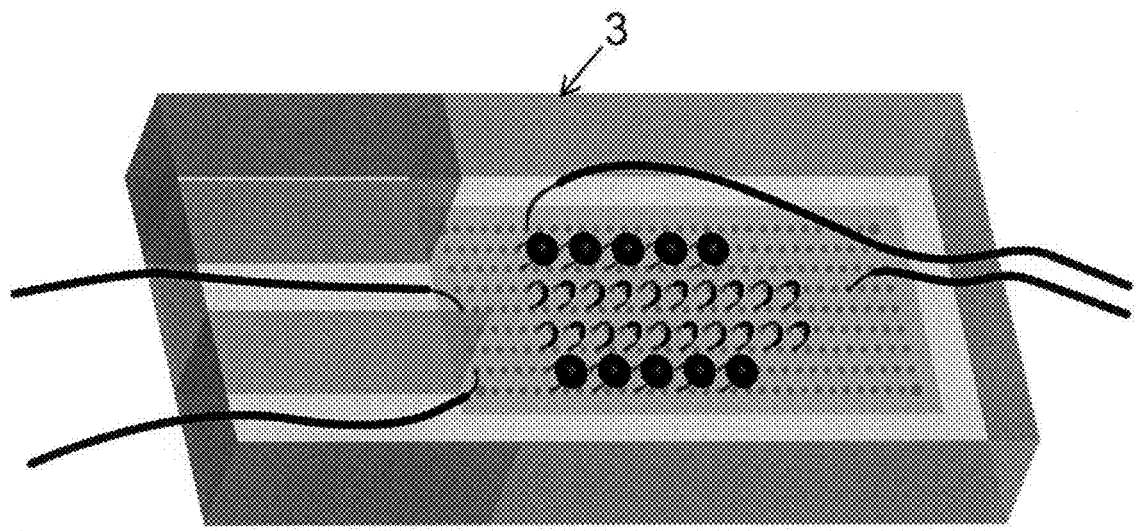

[Figure 3]
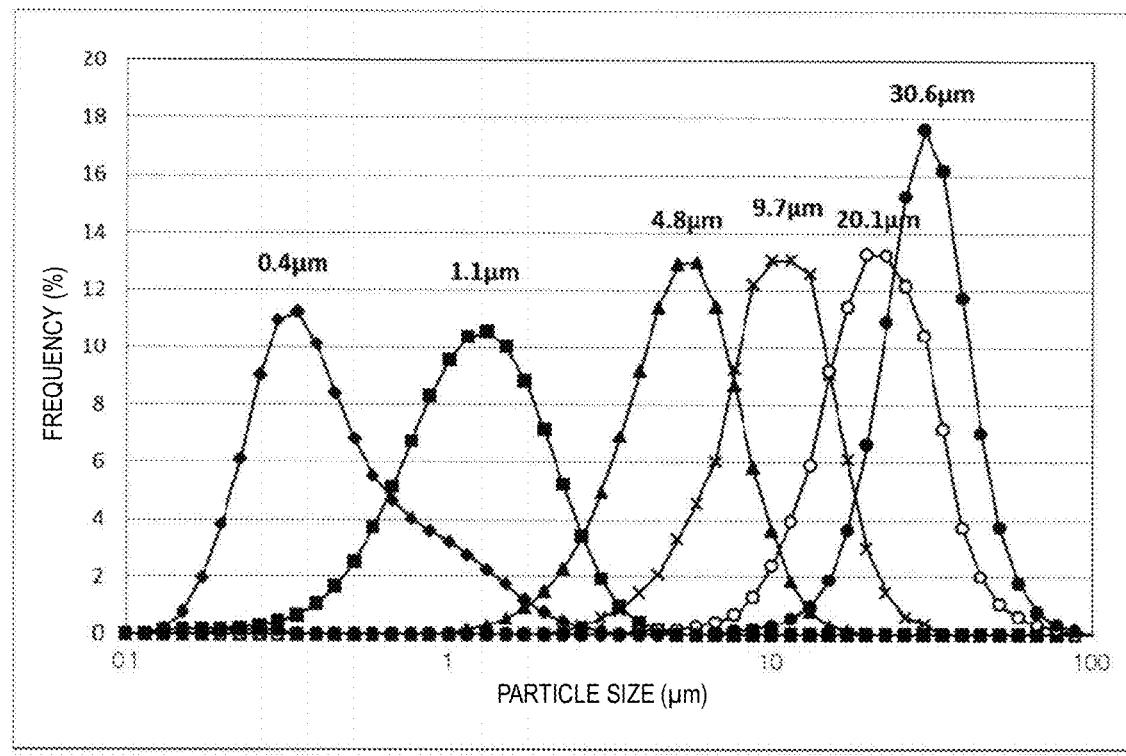

[Figure 4]
X-RAY POWDER DIFFRACTION DIAGRAMS OF FILM-FORMING POWDERS
<UNTREATED>
HAP
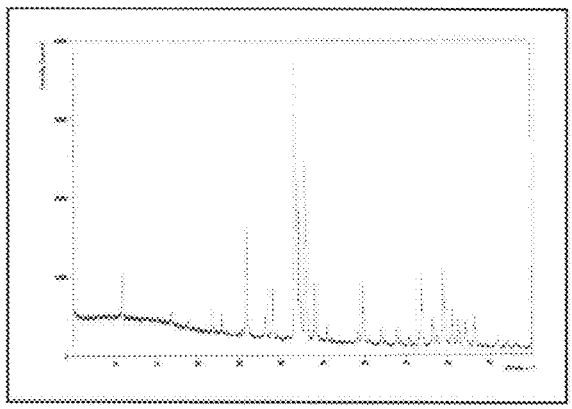
<MECHANICAL ENERGY TREATMENT → PLASMA TREATMENT (SEPARATE TREATMENTS)>
(1) HAP                                      (2) HAP + TITANIUM OXIDE (1% BLENDED)
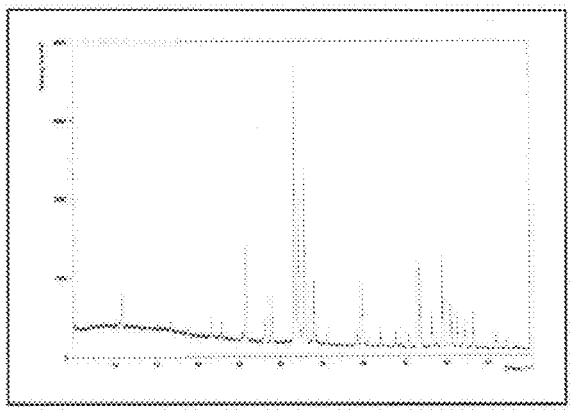 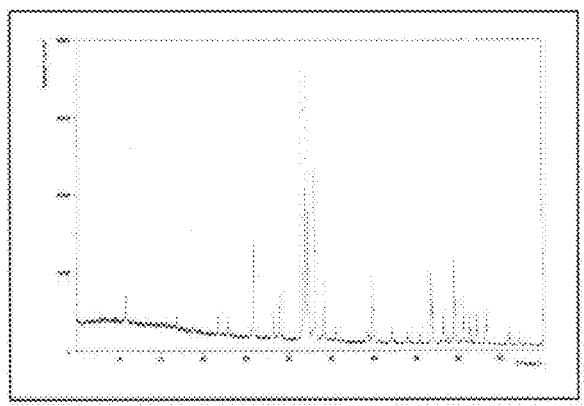

[Figure 5]
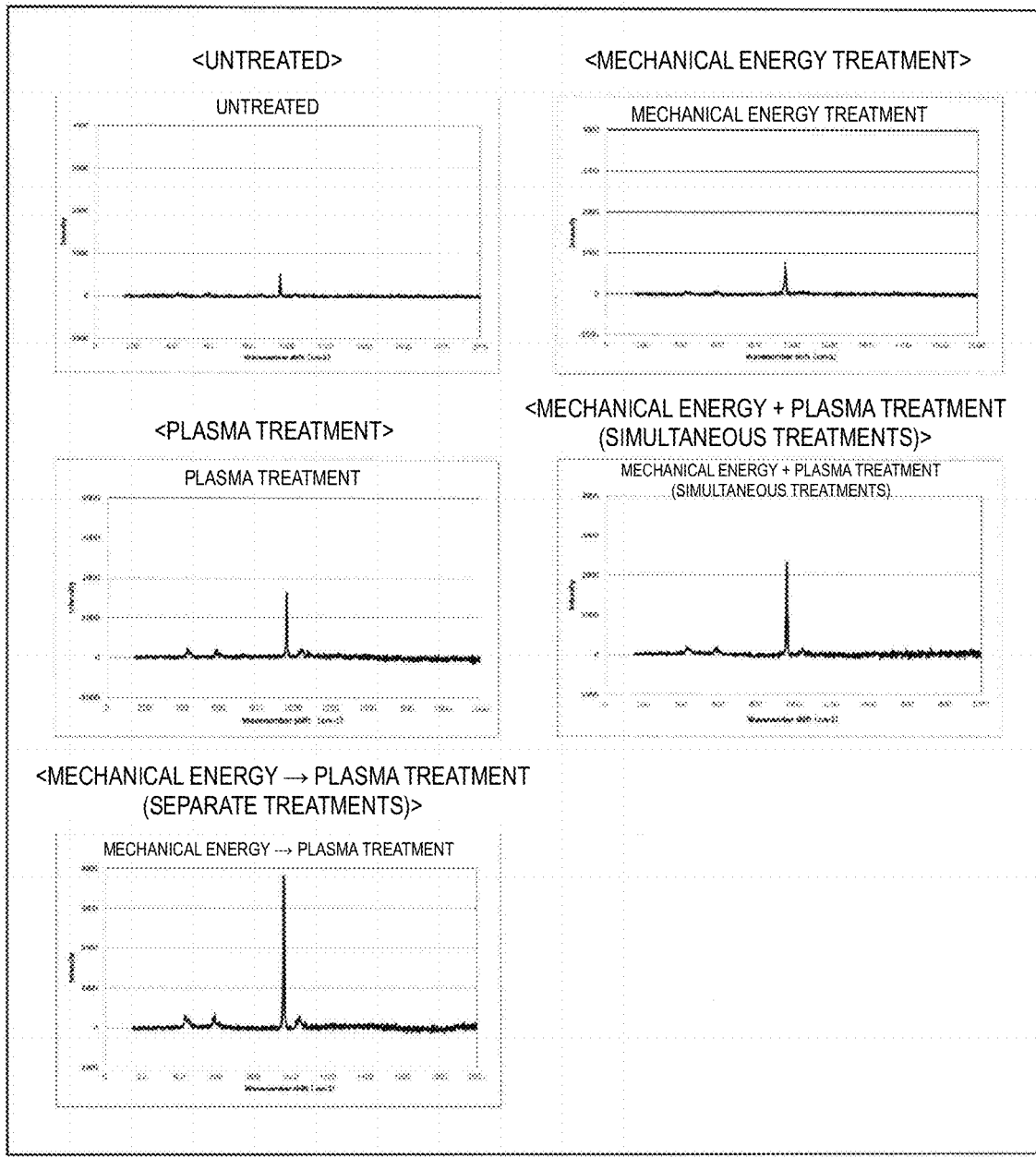

[Figure 6]
FORMED FILM LAYERS BY USING FILM-FORMING POWDERS IN WHICH COLOR TONE ADJUSTERS ARE BLENDED (CALCINED IN ARGON ATMOSPHERE) (PHOTOGRAPHS)
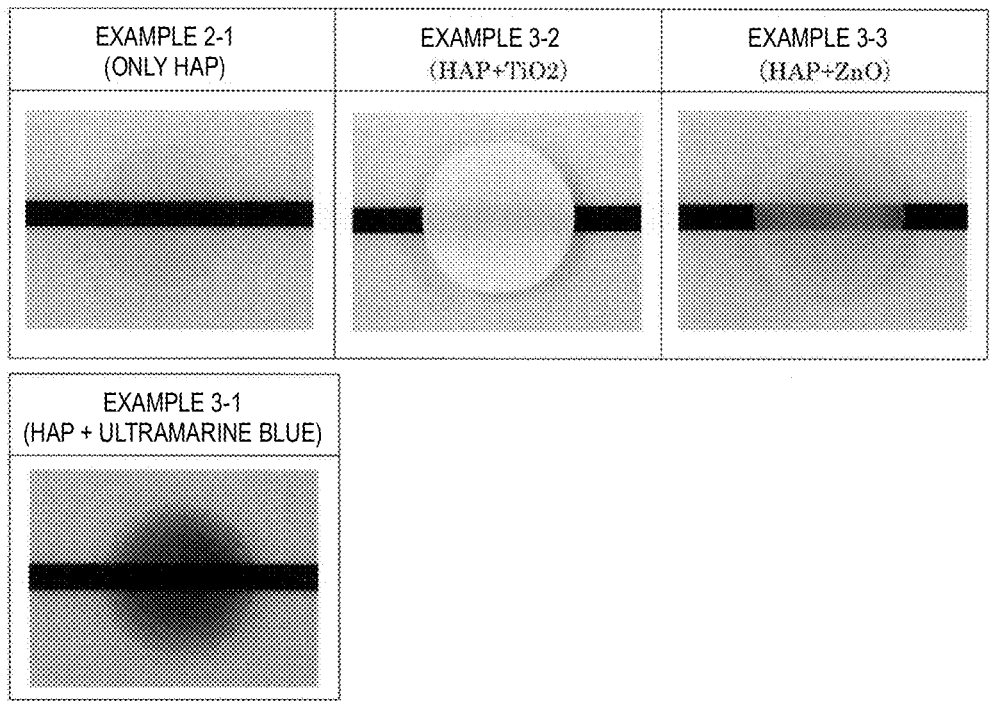
[Figure 7]
MULTILAYER OF FORMED FILM LAYERS BY USING FILM-FORMING POWDER AND FILM FORMING POWDERS IN WHICH COLOR TONE ADJUSTERS ARE BLENDED (PHOTOGRAPH)
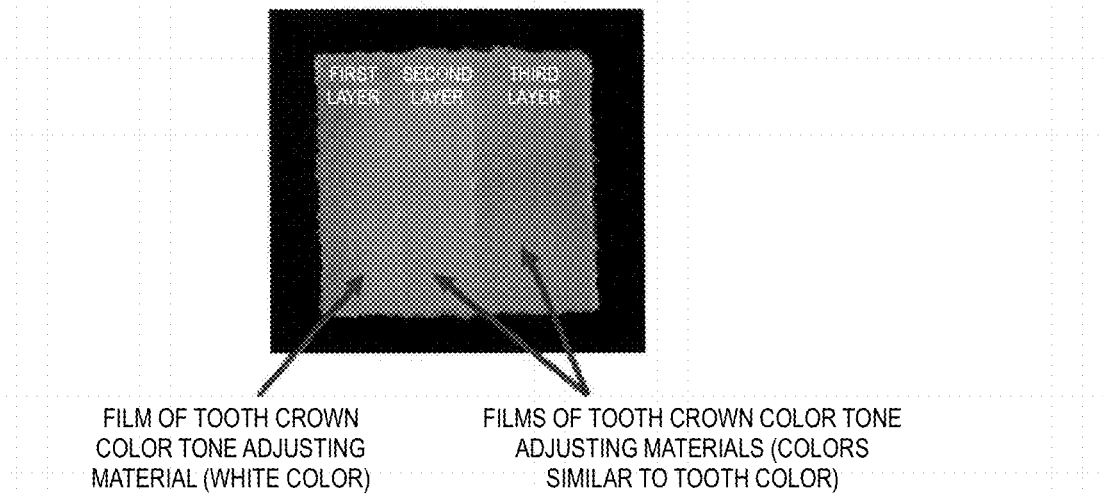

[Figure 8]

MULTILAYER OF FORMED FILM LAYERS BY USING FILM-FORMING POWDER AND FILM FORMING POWDERS IN WHICH COLOR TONE ADJUSTERS ARE BLENDED (CROSS SECTION IMAGE BY LASER MICROSCOPE)

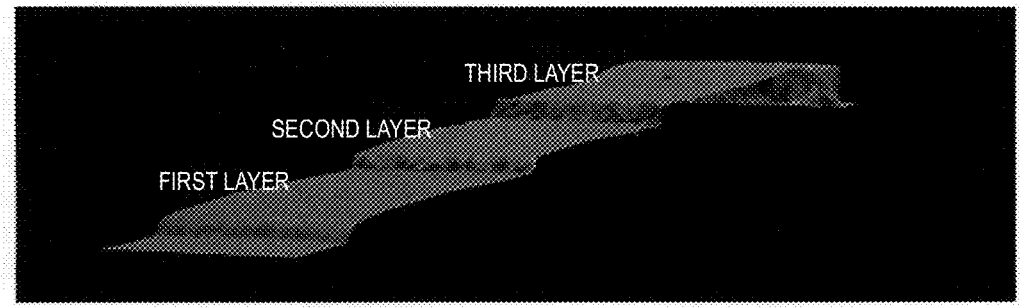

[Figure 9]

FORMED FILM LAYERS FORMED ON SURFACE OF TEETH WITH FILM-FORMING POWDERS IN WHICH COLOR TONE ADJUSTER ARE BLENDED AND WHICH ARE PRODUCED IN EXAMPLE 2-4 (PHOTOGRAPHS)

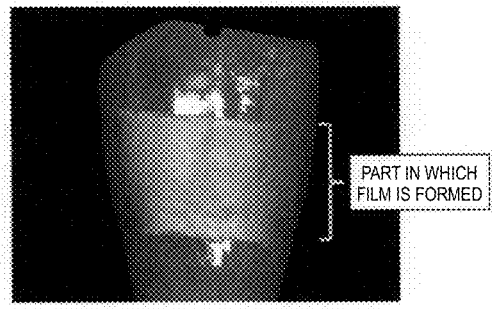

FORMED FILM LAYER <1% OF TITANIUM OXIDE BLENDED>

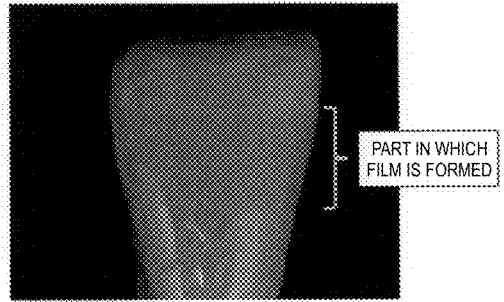

FORMED FILM LAYER <5% OF ZINC OXIDE BLENDED>

TOOTH-SURFACE-MEMBRANE-FORMING POWDER CONTAINING SINTERED APATITE

CROSS REFERENCE TO RELATED APPLICATIONS

This application is a National Stage of International Application No. PCT/JP2016/003297 filed on Jul. 12, 2016, which claims priority to Japanese Application No. 2015-139692 filed Jul. 13, 2015, the contents of which are hereby incorporated by reference in their entirety.

TECHNICAL FIELD

The present invention relates to: a film-forming powder comprising a powder of hydroxyapatite which is a main component of teeth, the powder being used in a device for forming a film on a surface of a tooth by spraying the powder on the tooth, and being suitable for forming a film having a high hardness and extremely low solubility in acid on the surface of a tooth in a short period of time; and a film-forming powder comprising a hydroxyapatite powder to which a color tone adjuster for adjusting the color tone of a tooth crown is blended, the powder being suitable for forming a film conforming to the color tone of a tooth in a short period of time.

BACKGROUND ART

Since apatite, particularly hydroxyapatite is a main component constituting teeth and bones, has excellent biocompatibility and is a suitable material for replacing and restoring damaged hard tissue, dental and medical materials comprising hydroxyapatite have been developed in recent years. In dentistry, for the prevention and the treatment of tooth decay and the whitening of teeth, a dentifrice comprising hydroxyapatite (Patent Documents 1 and 2), a glass powder for glass ionomer cement, comprising hydroxyapatite (Patent Document 3) and a whitening agent of teeth that is applied as a dental paste by mixing a hydroxyapatite powder and a strong acid aqueous solution (Patent Document 4) have been developed.

Although plasma spraying (Patent Document 5), sputtering (Patent Document 6), and a thermal decomposition method (Patent Documents 7 and 8) are disclosed as a method for forming calcium phosphate compound layers, these are not methods enabling coating directly teeth in the mouth.

Meanwhile, devices for spraying powders of hydroxyapatite, which is the main component of enamel or dentine, on the surfaces of teeth at high speeds and forming a hydroxyapatite film on the surface of enamel or dentine (Patent Documents 9 to 12) are proposed as methods enabling integrating the hydroxyapatite film with enamel or dentine.

It is recognized that the use of techniques in which a powder like the present invention is sprayed on a target enables forming a layer of hydroxyapatite powder also on the surface of a metal. For example, the uniform coating of the surface of an implant body with hydroxyapatite enables improving the biocompatibility and also contributes adequately to the prevention of inflammation around the implant, long-term stabilization in the convalescence of a treatment, and improvement in maintainability.

As described above, methods for spraying powders of hydroxyapatite, which is the main component of enamel or dentine, on the surfaces of teeth at high speeds and forming hydroxyapatite films on the surface of enamel or dentine have been investigated as methods for integrating with enamel or dentine. However, since the efficiency of film formation is not enough to form hydroxyapatite films on the surface of enamel or dentine and integrate the hydroxyapatite films with the enamel or the dentine relative to the amount of sprayed powder and it takes a long time to form a film, and the formed films are highly soluble in acid, the methods have not been put in practical use yet.

There are patient demands for aesthetic dental treatments that are growing in recent years behind the background of the present invention. There are treatments by a bleaching method or a porcelain lamination veneer method as methods for treatment. However, heavy burdens of patients due to these invasive treatments of healthy dentine are regarded as a problem. Meanwhile, since forming films on teeth by spraying a hydroxyapatite powder enables adjusting the color tones of tooth crowns with the same component as teeth, this enables treatments without invasion of healthy dentine, and conversely reinforcing dentine, with which the burdens of patients can be greatly reduced.

However, although devices and methods for spraying hydroxyapatite powders on the surfaces of teeth at high speeds and forming hydroxyapatite films on the surface of enamel or dentine have been proposed until now, apatite powders for forming films having a high hardness and extremely low solubility in acid in a short period of time or hydroxyapatite powders as color tone adjusting materials to use for aesthetic treatments, that are suitable to the color tones of various teeth have not been proposed.

Additionally, apatite powders for forming films having a high hardness and extremely low solubility in acid in a short period of time and these color tone adjusting materials have been produced only by common calcining, grinding, mixing, and the like. The production methods thereof have not been investigated in detail. In particular, methods for producing color tone adjusting materials have been performed by mixing powders by a powder-mixing machine or the like. However, in the case of methods involving mixing operation alone, when the composition varies due to insufficient mixing of powders or the like, it is considered that problems such as the color tones of formed films becoming uneven and the occurrence of color deterioration occur.

The Vickers hardness of the enamel of teeth is reported to be 270 to 366 Hv according to Dental Tools and Materials Investigation and Research Committee of The Japanese Society for Dental Materials and Devices. Moreover, it is reported that the properties of tooth crown restorations are required to be equivalent to the physical properties of dentine or better than the physical properties of dentine (Non-patent Document 1). In addition, there is also a report of plasma irradiation (Non-patent Documents 2 to 4).

PRIOR ART DOCUMENTS

Patent Documents

Patent Document 1: Japanese Patent No. 4040705
Patent Document 2: Japanese Patent No. 3971877
Patent Document 3: Japanese Patent No. 672112
Patent Document 4: Japanese Patent No. 3340265
Patent Document 5: Japanese unexamined Patent Application Publication No. 2014-50610
Patent Document 6: Japanese unexamined Patent Application Publication No. 2005-76113
Patent Document 7: Japanese unexamined Patent Application Publication No. 1-086975

Patent Document 8: Japanese unexamined Patent Application Publication No. 2001-178813
Patent Document 9: Japanese Patent No. 5031398
Patent Document 10: Japanese Patent No. 3962061
Patent Document 11: Japanese unexamined Patent Application Publication No. 2015-13095
Patent Document 12: Japanese unexamined Patent Application Publication No. 2015-104429

Non-Patent Documents

Non-patent Document 1: Dental Tools and Materials Investigation and Research Committee, "Shikashuufukubutsu ni Nozomareru Butsuriteki, Kikaiteki Seishitsu no Tekiseichi ni Tsuite (Appropriate Values of Physical and Mechanical Properties that Dental Restorations Are Expected to Have)", Dental Materials and Instruments, 16 (6), 555-562, 1997
Non-patent Document 2: Katsuhisa Kitano and 5 others, Taikiatsu Purazuma wo Tsuketemiyou (Let's Generate Atmospheric Pressure Plasma), J. Plasma Fusion Res. Vol. 84, No. 1, 19-28, 2008
Non-patent Document 3: Hiroshi Akamatsu and 2 others, Kantanni Hajimerareru Taikiatsu Purazuma Jetto no Jikken (Experiments on Atmospheric Pressure Plasma Jet That Can Be Easily Begun), Research Bulletin of Kobe City College of Technology No. 50 (2012)
Non-patent Document 4: Noboru Shiratori and 2 others, Taikiatsu Purazuma no Kenkyuu—Kagakukyouikuyou Ryuushikasokuki no Kenkyuu—(Research in Atmospheric Pressure Plasma—Research in Particle Accelerator for Science Education—), Research Result Report of Nagano Prefecture School Science Education Encouragement Fund collaborating with Tokyo Institute of Technology in 2013

SUMMARY OF THE INVENTION

Object to be Solved by the Invention

The object of the present invention is to solve the above-mentioned problems and to provide a film-forming powder for rapidly forming a film having a high hardness and extremely low solubility in acid on a substrate such as the surface of a tooth and additionally enabling adjusting the color tone to the same tone as the tooth.

Means to Solve the Object

The present inventors have developed a film-forming powder obtained by calcining a hydroxyapatite powder by using an inert gas; a film-forming powder obtained by adding and mixing a color tone adjuster for adjusting the color tone of a tooth crown to the film-forming powder; film-forming powders enabling forming a hydroxyapatite film having high strength and additionally low solubility in acid, and a hydroxyapatite film enabling adjusting the color tone of a tooth crown on a substrate such as the surface of a tooth in a short period of time by irradiating the above-mentioned film-forming powders with plasma using a low-temperature plasma treatment device in order to clean and activate the surfaces of particles and additionally applying mechanical energy such as compression or shearing. When a film-forming powder of the present invention is used, film formation is good relative to the amount of sprayed powder. Therefore, a film can be formed in a short period of time, little powder is scattered, and patients and dentists are subject to little adverse effect.

That is, the present invention is as follows:
(1) A film-forming powder for forming a film on a surface of a tooth for use in a jet-device for a tooth, the powder having a mean particle size of 0.5 to 30 μm, wherein the film-forming powder is produced by calcining an apatite represented by $Ca_{10-X} \cdot M_X(ZO_4)_6 Y_2$ (wherein X represents 0 to 10; M represents a metal or hydrogen; $ZO_4$ represents $PO_4$, $CO_3$, $CrO_4$, $AsO_4$, $VO_4$, $SiO_4$, $SO_4$ or $GeO_4$; and Y represents a hydroxyl group, a halogen element or a carbonate group) in an inert gas atmosphere at 600 to 1350° C.;
(2) The film-forming powder according to the above-mentioned (1), wherein the apatite is hydroxyapatite;
(3) The film-forming powder according to the above-mentioned (1) or (2), wherein the inert gas is argon gas or nitrogen gas;
(4) The film-forming powder according to any one of the above-mentioned (1) to (3), wherein a color tone adjuster for adjusting a color tone of a tooth crown is further blended in the film-forming powder;
(5) The film-forming powder according to the above-mentioned (4), wherein the color tone adjuster of a tooth crown is at least one selected from titanium oxide, zinc oxide, and ultramarine blue and a red pigment;
(6) The film-forming powder according to any one of the above-mentioned (1) to (5), wherein the film-forming powder is produced by plasma irradiation;
(7) The film-forming powder according to the above-mentioned (6), wherein the film-forming powder is produced by further applying mechanical energy;
(8) The film-forming powder according to the above-mentioned (7), wherein the film-forming powder is produced by application of mechanical energy followed by plasma irradiation;
(9) The film-forming powder according to any one of the above-mentioned (6) to (8), wherein the plasma irradiation is plasma irradiation in which helium gas is used as an irradiation gas;
(10) The film-forming powder according to any one of the above-mentioned (1) to (9), wherein a film thickness of a formed film is 30 μm or more, and Vickers hardness is 340 Hv or more when the powder is sprayed on a substrate under conditions of an inner diameter of a handpiece tip nozzle of 0.5 to 5.0 mm, a spray pressure of 0.2 to 0.8 MPa, a distance between a spray nozzle tip and the substrate of 0.1 to 3.0 cm, and a moving speed of the spray nozzle of 0 to 10 mm/s;
(11) A method for producing a film-forming powder for forming a film on a surface of a tooth for use in a jet-device for a tooth, the powder having a mean particle size of 0.5 to 30 μm, comprising calcining an apatite represented by $Ca_{10-X} \cdot M_X(ZO_4)_6 Y_2$ (wherein X represents 0 to 10; M represents a metal or hydrogen; $ZO_4$ represents $PO_4$, $CO_3$, $CrO_4$, $AsO_4$, $VO_4$, $SiO_4$, $SO_4$ or $GeO_4$; and Y represents a hydroxyl group, a halogen element or a carbonate group) in an inert gas atmosphere at 600 to 1350° C., and then performing grinding and classification;
(12) The method for producing a film-forming powder according to the above-mentioned (11), wherein the apatite is hydroxyapatite;
(13) The method for producing a film-forming powder according to the above-mentioned (11) or (12), wherein the inert gas is argon gas or nitrogen gas;
(14) The method for producing a film-forming powder according to any one of the above-mentioned (11) to (13), comprising further blending a color tone adjuster for adjusting a color tone of a tooth crown;
(15) The method for producing a film-forming powder according to the above-mentioned (14), wherein the color tone adjuster of a tooth crown is at least one selected from titanium oxide, zinc oxide, ultramarine blue and a red pigment;

(16) The method for producing a film-forming powder according to any one of the above-mentioned (11) to (15), comprising further performing plasma irradiation after grinding and classification;

(17) The method for producing a film-forming powder according to the above-mentioned (16), comprising further applying mechanical energy;

(18) The method for producing a film-forming powder according to the above-mentioned (17), wherein plasma irradiation is performed after applying mechanical energy;

(19) The method for producing a film-forming powder according to any one of the above-mentioned (16) to (18), wherein the plasma irradiation is plasma irradiation in which helium gas is used as an irradiation gas;

(20) The method for producing a film-forming powder according to any one of the above-mentioned (11) to (19), wherein a film thickness of a formed film is 30 μm or more, and Vickers hardness is 340 Hv or more when the powder is sprayed on a substrate under conditions of an inner diameter of a handpiece tip nozzle of 0.5 to 5.0 mm, a spray pressure of 0.2 to 0.8 MPa, a distance between a spray nozzle tip and a substrate of 0.1 to 3.0 cm, and a moving speed of the spray nozzle of 0 to 10 mm/s; and

(21) A pellet comprising the film-forming powder according to any one of the above-mentioned (1) to (10).

Different aspects of the present invention include: [1] a method for forming a film on a surface of a tooth comprising using a film-forming powder having a mean particle size of 0.5 to 30 μm that is produced by calcining the above-mentioned apatite represented by $Ca_{10-X}.M_X(ZO_4)_6Y_2$ in an inert gas atmosphere at 600 to 1350° C., in a jet-device for a tooth; [2] a film-forming powder having a mean particle size of 0.5 to 30 μm produced by calcining the above-mentioned apatite represented by $Ca_{10-X}.M_X(ZO_4)_6Y_2$ in an inert gas atmosphere at 600 to 1350° C., for use as a film-forming powder for forming a film on the surface of a tooth, the powder being used in a jet-device for a tooth, and; [3] use of a powder having a mean particle size of 0.5 to 30 μm produced by calcining the above-mentioned apatite represented by $Ca_{10-X}.M_X(ZO_4)_6Y_2$ in an inert gas atmosphere at 600 to 1350° C., in the production of a film-forming powder for forming a film on the surface of a tooth, the powder being used in a jet-device for a tooth; and [4] a film-forming powder having a mean particle size of 0.5 to 30 μm for forming a film on the surface of a tooth, the powder being used in a jet-device for a tooth, wherein the film-forming powder is produced by calcining an apatite represented by $Ca_{10-X}.M_X(ZO_4)_6Y_2$ at 600 to 1350° C. followed by plasma irradiation.

Effect of the Invention

Since an apatite film can be formed rapidly without giving a patient a burden by spraying a film-forming powder of the present invention on the surface of a tooth at a high speed, the prevention and the treatment of tooth decay, the whitening of teeth, and aesthetic treatment by a film similar in the color tone to the surface of a tooth can be performed easily. A formed film layer of only hydroxyapatite becomes translucent. Therefore, when films are formed on tooth decay parts, hyperesthetic parts or exposed root surface parts, sites to be treated are difficult to see. Therefore, it is important to color a formed film layer in order to define the area to be treated.

According to the present invention, since the suppression of the solubility of a formed film layer and improvement in hardness were confirmed, it is possible to obtain a film that is maintained stably for a long period of time, specifically a film-forming powder in which a color tone adjuster that is preferable to obtain a film such that the color unevenness of a formed film layer is suppressed, and the color tone is stabilized is blended. This also enables forming formed film layers of various hues that patients individually desire on the surfaces of the teeth of the patients worrying about the hues of the teeth. This contributes greatly to esthetic dental treatment.

BRIEF DESCRIPTION OF THE DRAWINGS

FIG. 1 is a figure illustrating a plasma generator used for the present invention.

FIG. 2 is a figure illustrating a high voltage-generating circuit in the plasma generator used for the present invention.

FIG. 3 is a chart showing the mean particle sizes and the particle size distributions of film-forming hydroxyapatite powders produced in Example 2-1.

FIG. 4 is a diagram showing diffraction patterns by a powder X-ray diffractometer of Example 9-1.

FIG. 5 is a figure illustrating changes in the spectrum of a film-forming powder of Example 9-2 by a laser Raman spectrometer.

FIG. 6 is formed film layers comprising film-forming powders in which color tone adjusters are blended (photographs).

FIG. 7 is a figure (photograph) of a multilayer of formed film layers comprising a film-forming powder produced in Example 2 and film-forming powders in which color tone adjusters are blended (1% of titanium oxide is blended in a first layer, 5% of zinc oxide is blended in a second layer, and a third layer is hydroxyapatite).

FIG. 8 is a figure illustrating the cross section image of the multilayer of the formed film layers illustrated in FIG. 7 by a laser microscope.

FIG. 9 is formed film layers formed on the surfaces of teeth by using film-forming powders in which color tone adjusters of Example 2-4 are blended (1% of titanium oxide blended (left figure), and 5% of zinc oxide blended (right figure) (photographs).

MODE OF CARRYING OUT THE INVENTION

A film-forming powder of the present invention is a powder having a mean particle size of 0.5 to 30 μm for use in a jet-device for teeth, the powder being used in the application of forming a film on the surface of a tooth, wherein the film-forming powder is produced by calcining an apatite represented by $Ca_{10-X}.M_X(ZO_4)_6Y_2$ (wherein X represents 0 to 10; M represents a metal or hydrogen; $ZO_4$ represents $PO_4$, $CO_3$, $CrO_4$, $AsO_4$, $VO_4$, $SiO_4$, $SO_4$ or $GeO_4$; and Y represents a hydroxyl group, a halogen element or a carbonate group) in an inert gas atmosphere at 600 to 1350° C. A method for producing the film-forming powder, according to the present invention is not particularly limited as long as the method is a method for producing a film-forming powder having a mean particle size of 0.5 to 30 μm, for use in a device for forming a film on the surface of a tooth by spraying a powder on the tooth, by calcining the above-mentioned apatite represented by $Ca_{10-X}.M_X(ZO_4)_6Y_2$ in an inert gas atmosphere at 600 to 1350° C., followed by grinding and classifying. A calcium phosphate-based apatite is preferable as the above-mentioned apatite, and the above-mentioned apatite particularly preferably includes hydroxyapatite, which is a basic calcium phosphate represented by the chemical formula $Ca_{10}(PO_4)_6(OH)_2$.

Even though the molar ratio Ca/P is a nonstoichiometric ratio that is not 1.67 in the above-mentioned calcium phosphate-based apatite, the apatite exhibits the characteristics of an apatite, and can have an apatite structure, an apatite in the present invention include also such a synthetic apatite in which, for example, the molar ratio Ca/P is around 1.4 to 1.8.

The above-mentioned hydroxyapatite is one type of calcium phosphate and has good biocompatibility, and is contained in a large amount in bones, teeth and the like. Hydroxyapatite can be obtained from fish bones of edible fish such as salmon, pork bones, cow bones and the like as natural hard tissue besides hydroxyapatite synthesized by the usual method.

A method for synthesizing hydroxyapatite used for the present invention is not particularly limited and can be selected properly. For example, hydroxyapatite can be obtained by reacting a calcium salt with a phosphate in an aqueous solution and drying at a prescribed temperature. The calcium salt includes a common calcium salt such as calcium hydroxide, calcium acetate, calcium carbonate, calcium chloride, calcium citrate and calcium lactate. The phosphate includes a common phosphate such as phosphoric acid, ammonium phosphate, sodium phosphate, potassium phosphate, pyrophosphoric acid and sodium hexametaphosphate.

Other synthesizing methods include a method in which calcium nitrate tetrahydrate is dissolved in pure water, and then the pH of this solution is adjusted to 10 with aqueous ammonia, and thereafter the solution thus obtained is slowly added with an aqueous ammonium dihydrogen phosphate solution, and at that time, a small amount of aqueous ammonia is added thereto so that the pH becomes 10, all the aqueous diammonium hydrogen phosphate solution is added, thereafter the solution is aged at 90° C. by stirring the solution, a precipitate is filtered and washed in pure water by ultrasonication washing, and the obtained solid matter is dried at 80° C.

Other synthesizing methods include a method in which an aqueous phosphoric acid solution is dropped at room temperature into aqueous 0.5 M calcium hydroxide suspension to produce a suspension of an apatite, the pH of the reaction solution is adjusted to 10.5 with an aqueous ammonia solution, it is confirmed that the solution has been mixed thoroughly, thereafter this suspension is aged overnight, the obtained precipitate is filtered, and the solid matter is dried at 80° C.

In addition, hydroxyapatite can also be properly synthesized in a usual production method by adding pure water to calcium hydrogen phosphate dihydrate and calcium carbonate, mixing and grinding the mixture by an automatic mortar, drying the obtained mixed powder at 80° C. and the like.

In case of synthesizing an apatite in which Y in the formula is a halogen element, by producing hydroxyapatite in the copresence of a source of the halogen element such as calcium fluoride, sodium fluoride or calcium chloride, the hydroxyl groups of the hydroxyapatite can be substituted with the halogen element, to produce fluorine apatite $Ca_{10}(PO_4)_6F_2$ and chloride apatite $Ca_{10}(PO_4)_6Cl_2$ in which Y is a halogen element. The substitution can also be performed by forming hydroxyapatite followed by mixing with a solvent comprising a halogen element source. A halogen-substituted apatite can also be synthesized by performing the dry synthesis of hydroxyapatite from a halogen compound such as calcium fluoride and a phosphate compound. Fluorine apatite with fluorine substitution can be used as a tooth surface-reinforcing agent.

Similarly, hydroxyapatite may be produced in the copresence of a compound comprising carbonate groups such as carbon dioxide gas, dry ice, sodium hydrogen carbonate, disodium carbonate, potassium hydrogen carbonate, dipotassium carbonate, ammonium hydrogen carbonate, diammonium carbonate and calcium carbonate, so that the hydroxyl groups for Y can be substituted with carbonate groups, to synthesize carbonate apatite.

Similarly, when Ca is substituted with a metal element, namely, when x is not 0 in the formula, an apatite in which at least a part of Ca is substituted with a metal element can be synthesized by making a water soluble salt such as sodium, lithium, magnesium, barium, strontium, zinc, cadmium, lead, vanadium, silicon, germanium, iron, arsenic, manganese, aluminium, rare earth elements, cobalt, silver, chromium, antimony, tungsten and molybdenum coexist at the time of producing hydroxyapatite.

A film-forming powder of the present invention can be obtained, for example, by calcining an apatite such as hydroxyapatite produced by common methods as mentioned above in an inert gas atmosphere at 600 to 1350° C., preferably at 800 to 1350° C. A film-forming powder having a mean particle size of 0.5 to 30 μm, preferably 1 to 10 μm can be obtained by calcining an apatite in an inert gas atmosphere at 600 to 1350° C., thereafter grinding and classifying, preferably grinding, classifying and mixing. As long as the mean particle size is 0.5 to 30 μm, the shape, the structure and the like thereof are not particularly limited, and can be selected properly according to an object. A powder more suitable for forming a film can be obtained by performing the treatment of plasma irradiation and further the treatment of application of mechanical energy on a film-forming powder obtained by the calcining.

As to a film-forming powder of the present invention, when the performance of a film formed on a substrate such as the surface of a tooth is investigated, it is revealed that the film-forming powder enables forming a film in a short period of time. When the capability to hide a discoloration of a tooth crown is examined additionally, it is revealed that it is preferable to form a film having a thickness of 30 μm or more and that it is preferable for the Vickers hardness to be 340 Hv or more. Therefore, it has become clear that it is necessary to calcine an apatite in an inert gas atmosphere at 600 to 1350° C. Color tone adjusters for adjusting the color tone of a tooth crown can be blended in a film-forming powder of the present invention. Film-forming powders in which color tone adjusters are blended for forming formed film layers imparting various color tones to teeth can be obtained by integrating a hydroxyapatite powder with various color tone adjusters.

Since a small amount of the above-mentioned color tone adjusters are used, the difference in the mean particle sizes thereof does not exert a great influence on the mixability in the mixture with hydroxyapatite. However, since it is preferable that the particle sizes of color tone adjusting materials are smaller than the particle size of hydroxyapatite or nearly equal to the particle size of hydroxyapatite, it is preferable that the particle sizes of color tone adjusting materials are 0.01 to 30 μm. Additionally in view of imparting better mixability, it is preferable that the particle sizes of color tone adjusting materials are 0.05 to 10 μm.

Known inorganic pigments and organic pigments as pigments for dental use can be used without any limitation for the color tone adjusters of tooth crowns. The inorganic pigments include an oxide, a hydroxide, a sulfide, a chromate, a silicate, a sulfate, a carbonate, a ferrocyanide compound, a phosphate and carbon, and particularly an oxide is preferably used. The organic pigments include a tar dye, an azo-based pigment, a phthalocyanine pigment, a condensed polycyclic pigment, a nitro-based pigment, a nitroso-based pigment, a fluorescent pigment, and particularly an azo-based pigment and a phthalocyanine pigment are preferably used. These inorganic pigments and organic pigments can be mixed and used.

Specifically, a white pigment includes titanium oxide, zinc oxide, zirconium oxide, magnesium oxide, aluminium oxide, barium sulfate and magnesium fluoride. A red pigment and/or a red dye includes iron oxide red, molybdate red, Cromophtal Red, Red No. 2 (Amaranth), Red No. 104 (Phloxine), Red No. 105 (Rose Bengal), Red No. 106 (Acid Red), Red No. 201 (Lithol Rubine B), Red No. 202 (Lithol Rubine BCA), Red No. 203 (Lake Red C), Red No. 204 (Lake Red CBA), Red No. 205 (Lithol Red), Red No. 206 (Lithol Red CA), Red No. 207 (Lithol Red BA), Red No. 208 (Lithol Red SR), Red No. 213 (Rhodamine B), Red No. 214 (Rhodamine B Acetate), Red No. 215 (Rhodamine B Stearate), Red No. 218 (Tetrachlorotetrabromofluorescein), Red No. 219 (Brilliant Lake Red R), Red No. 220 (Deep Maroon), Red No. 221 (Toluidine Red), Red No. 223 (Tetrabromofluorescein), Red No. 225(Sudan III), Red No. 226 (Helindone Pink CN), Red No. 227 (Fast Acid Magenta), Red No. 228 (Permaton Red), Red No. 230 (1) (Eosine YS), Red No. 230 (2) (Eosine YSK), Red No. 231 (Phloxine BK), Red No. 232(Rose Bengal K), Red No. 401(Violamine R), Red No. 404 (Brilliant Fast Scarlet), Red No. 405 (Permanent Red F5R), Red No. 501 (Scarlet Red N.F.), Red No. 502 (Ponceau 3R), Red No. 503 (Ponceau R), Red No. 504 (Ponceau SX), Red No. 505 (Oil Red XO), Red No. 506 (Fast Red S), Purple No. 201(Alizurine Purple Lake SS), Purple No. 401 (Alizurol Purple), Naphthol AS (Naphthol Rubin, Naphthol Red FGR, Naphthol Carmine FBB, Naphthol Carmine F3B, Naphthol Red F5RK and Naphthol Red HF4B), BONA Lake (BONA Barium Lake, BONA Calcium Lake, BONA Strontium Lake, BONA Manganese Lake, and BONA Magnesium Lake), Lithol Rubine (Brilliant Carmine 6B), Diaminoanthraquinonyl Red, DPP Red BO, diketo pyrrolo pyrrole, Perylene Red BL, Imidazolone Red HFT, Imidazolone Carmine HF3C, Benzimidazolone Carmine HF4C, Diaminoanthraquinonyl Red, Dichloroquinacridone Magenta, Quinacridone Magenta, Quinacridone Red, Quinacridone Violet, Dioxane Violet, and Condensed Azo Scarlet. A yellow pigment and/or a yellow dye includes yellow iron oxide, titan yellow, chrome oxide, bismuth oxide, Cromophtal Yellow, Yellow No. 4 (Tartrazine), yellow No. 201 (fluorescein), Yellow No. 202 (1) (Uranine), Yellow No. 202 (2) (Uranine K), Yellow No. 203 (Quinoline Yellow WS), Yellow No. 204 (Quinoline Yellow SS), Yellow No. 205 (Benzidine Yellow G), Yellow No. 401(Hansa Yellow), Yellow No. 402 (Polar Yellow 5G), Yellow No. 403 (1) (Naphthol Yellow S), Yellow No. 406 (Metanil Yellow), Yellow No. 407 (Fast Light Yellow 3G), Hansa Yellow 10G, Disazo Yellow (AAMX, AAOT, HR, 4G, 3A, GR and G), Benzimidazolone Yellow (H2G and HG), Isoindoline Yellow (G and R), Pyrazolone Yellow HGR, and Diarylide Yellow AAOA. A blue pigment and/or a blue dye includes Cobalt Blue, Ultramarine Blue, Berlin Blue, Cromophtal Blue, Phthalocyanine Blue, Aluminium Phthalocyanine Blue, Indanthrene Blue, Green No. 3 (Fast Green FCF), Blue No. 1 (Brilliant Blue FCF), Blue No. 2 (Indigo Carmine), Blue No. 201(Indigo), Blue No. 202 (Patent Blue NA), Blue No. 203 (Patent Blue CA), Blue No. 204 (Carbanthrene Blue), Blue No. 205 (Alphazurine FG). Additionally, a black pigment includes black iron oxide and carbon black.

Silicon dioxide and resin particulates (specifically a polymethyl acrylate powder, polyethylene spheres, polypropylene spheres, polystyrene spheres, nylon spheres and the like) can be used as color tone adjusters for giving a gloss.

In addition to the above-mentioned ingredients, other ingredients commonly used for dental materials, for example, silica, magnesium phosphate, calcium carbonate, zirconia or the like can be blended in a film-forming powder of the present invention if needed as long as the effects of the present invention are not spoiled.

The film-forming powder of the present invention further includes a powder having the same mean particle size or a mixture of powders different in particle size; a powder calcined in the same inert gas atmosphere, or a mixture of powders calcined in different inert gas atmospheres or a mixture of a powder calcined in an inert gas atmosphere and a powder calcined in the air atmosphere; a mixture of powders that are different in both the particle size and the calcining atmosphere; and a powder obtained by blending and calcining other ingredients than an apatite.

It is preferable that plasma irradiation by using a device for irradiation with plasma such as low-temperature plasma in the production of the film-forming powder of the present invention is performed in the treatment of mixing apatite powders or in the treatment of mixing an apatite powder and other powders such as color tone adjusters than apatites as well as in the treatment of an apatite powder alone. For example, also in a method for producing a hydroxyapatite powder in which color tone adjusters for adjusting the color tone of a tooth crown are blended, a treatment of mixing a hydroxyapatite powder and color tone adjusters is usually performed. However, it is preferable to perform mixing operation by using a device for irradiation with plasma such as low-temperature plasma at the time of mixing.

It is preferable to perform treatment by using a device for applying mechanical energy such as compression or shearing in addition to plasma irradiation. It is supposed that plasma irradiation enables cleaning and activating the surfaces of particles, and applying mechanical energy enables integrating particles strongly and closely or designing particles such that the functionality of powders is further enhanced. However, even though only treatment by a device for applying mechanical energy is performed as a result of examination, no change in the characteristics of the formed film was observed. A change in the physicochemical characteristics such as further enhanced crystallization of the surfaces of particles was confirmed by performing the treatment of applying mechanical energy in addition to these treatments by plasma irradiation, especially by performing plasma treatment after mechanical energy treatment is performed. Good results were found in the characteristics of a film formed by using a film-forming powder of the present invention on which the treatment of applying mechanical energy and the treatment of plasma irradiation were performed, and it was confirmed that a film suitable for use in the oral cavity environment could be formed.

As the above-mentioned plasma irradiating device, a plasma surface treatment device (Asakusa Machinery Co., LTD.), a multi-gas plasma jet (Plasma Factory Co., Ltd.), a plasma mixer PMR (ALPHA Corporation) or the like can be used. Changes in the structure, phase transition, reactivity, adsorptivity, catalytic activity and the like can be caused by applying mechanical energy such as grinding, friction, extension, compression and shearing to particles. As a device for applying such mechanical energy, a hybridization system (NARA MACHINERY CO., LTD.), Mechanofusion, Nobilta (Hosokawa Micron Corporation) or the like can be used. For example, Mechanofusion has the effect of smashing convex parts of particles by shearing force and the like and enables obtaining particles as if the particles were chamfered by grinding and reattachment. It becomes possible to produce a film-forming powder that is the optimal for film formation by using these devices.

In the case of irradiation with low-temperature plasma, which promotes the cleaning and activation of the surfaces of particles, it is preferable to set an applied voltage as 5 to 20 kV and the rotational speed of a rotor head as 1500 to 6000 rpm. The treatment time differs depending on treated powders and the like, and 5 to 20 minutes can be exemplified. As plasma gas types, helium gas, argon gas, oxygen gas, nitrogen gas, neon gas, carbon dioxide gas, air or the like can be used, and helium gas can be exemplified preferably. In the case of treatment with a device for applying mechanical energy, it is preferable to set the rotational speed of a rotor head giving compression and shear force at 100 to 6000 rpm. The treatment time depends on treated powders and the like, and 5 to 30 minutes can be exemplified. The applied voltage, the type of gas, the treatment speed, the treatment time and the like of the plasma irradiating device and the device for applying mechanical energy can be changed properly. The form of the film-forming powder is optionally the forms of a pellet into which a powder is pressed and a calcined pellet obtained by further calcining this pellet as well as a powder, and these pellets can also be used as powders by grinding and scraping the pellets. The form of the pellet is optionally a pellet form into which one film-forming powder is made or a pellet obtained by layering two or more types of film-forming powders. These forms are included in the present invention for convenience.

The film-forming powder of the present invention is used in the applications for forming a film on the surface of a tooth by using the film-forming powder in a jet-device for a tooth. As such devices for forming a film spraying a powder, jet-devices for spraying a powder described in Patent Documents 9 to 12 or the like can be used. Examples of conditions for forming a film in the case of using a self-manufactured jet-device for spraying a powder include the inner diameter of a handpiece tip nozzle: 0.5 to 5.0 mm, the spray pressure: 0.2 to 0.8 MPa, the distance between a spray nozzle tip and the surface of a tooth: 0.1 to 30 mm (with the nozzle tip supported perpendicularly to the surface of a tooth), and the moving speed of the spray nozzle: 0 to 10 mm/s. The jet-devices for spraying a powder, described in the Patent Documents 9 to 12 can be used under the same conditions. It is preferable that the surface of the obtained formed film layer is polished with a diamond polisher paste. A multilayer of formed film layers can be formed on the surface of a tooth crown by forming a film by using a film-forming powder in which color tone adjusters are blended, thereafter forming other films by using a film-forming powder in which other color tone adjusters are blended or in which color tone adjusters are not blended as the upper layers thereof.

EXAMPLES

Although this invention will be described by Examples hereinbelow, this invention is not limited by the following Examples in any meaning.

Example 1

[Synthesis of Apatites]
1-1 Synthesis of Hydroxyapatite

A suspension of an apatite was produced by dropping an aqueous 0.3 M phosphoric acid solution (2 L) into an aqueous 0.5 M calcium hydroxide suspension (2 L) at room temperature. The pH of the reaction solution was adjusted to 10.5 by using aqueous ammonia solution. It is confirmed that the solution has been mixed thoroughly, and thereafter, this suspension was aged overnight. The obtained precipitate was filtered, and the solid matter was dried at 80° C.

1-2 Synthesis of Fluorine Apatite

An aqueous solution (2 L) was prepared by mixing 0.3 mol of phosphoric acid and 0.1 mol of hydrogen fluoride with 0.25 M calcium hydroxide suspension (2 L). The mixed aqueous solution of phosphoric acid and hydrogen fluoride was dropped into this calcium hydroxide suspension for 2 hours at room temperature. After the dropping was finished, the suspension was aged at 80° C. for 5 hours with the suspension stirred. The obtained precipitate was filtered, and the solid matter was dried at 80° C.

1-3 Synthesis of Carbonate Apatite

For 30 minutes, 0.75 L of pure water was bubbled by a carbon dioxide gas. The pH of this solution decreased from 7 to 4. To the obtained solution was added 0.3 mol of phosphoric acid, and the total volume was scaled up to 1 L with pure water. This solution was dropped at a rate of 1 L/3h into an aqueous 0.5 M calcium hydroxide solution (1 L). The suspension was stirred for 2 hours. Thereafter, the mixture was aged overnight and filtered, and the obtained solid matter was dried at 80° C.

1-4 Synthesis of Magnesium-Solid Solution Apatite

In 500 mL of pure water, 0.19 mol of calcium nitrate tetrahydrate and 0.01 mol of $Mg(OH)_2$ were dissolved. Then, the pH of the solution was adjusted to pH 10 with aqueous ammonia. An aqueous 0.12 M ammonium dihydrogen phosphate solution (500 mL) was slowly added to this solution. At this time, a small amount of aqueous ammonia was added so that the pH of the solution was adjusted to 10. All the aqueous diammonium hydrogen phosphate solution was added, and thereafter the solution was aged at 90° C. for 5 hours with the solution stirred. A precipitate was filtered and washed in pure water by ultrasonication treatment 3 times. The obtained solid matter was dried at 80° C.

Example 2

[Preparation of Film-Forming Powders]

As an atmosphere furnace for calcining, a vacuum purge atmosphere furnace 2024-V (MARUSHO DENKI CO., LTD.) was used. As a device for grinding and classifying, the fluidized bed counter jet mill Counter Jet Mill 100 AFG (HOSOKAWA MICRON CORPORATION) was used.

2-1 Film-Forming Apatite Powders

Hydroxyapatite, fluorine apatite, carbonate apatite and magnesium-solid solution apatite synthesized as described above were ground with a mortar and calcined in the air, an argon gas atmosphere or a nitrogen gas atmosphere at 200 to 1350° C. or 600 to 1350° C. The calcined samples were ground and classified with a counter air flow mill to obtain hydroxyapatite powders of the respective samples, having a mean particle size of 0.5 to 30 μm.

2-2 Film-Forming Hydroxyapatite Powders in which Silica was Blended

As an ingredient other than apatites, 1% by weight of silica was added to the film-forming apatite powders synthesized in the above 2-1, and the same treatment was performed to obtain hydroxyapatite powders in which silica was blended. Silica that was "Sciqas series produced by SAKAI CHEMICAL INDUSTRY CO., LTD., particle size: 1.0 μm" was used.

2-3 Film-Forming Hydroxyapatite Powders in which Color Tone Adjuster was Blended Various color tone adjusters were blended in the film-forming hydroxyapatite powders produced in the above 2-1 to obtain film-forming powders in which the color tone adjusters were blended. Titanium oxide that was "specially produced by KISHIDA CHEMICAL Co., Ltd.", zinc oxide that was "an official zinc oxide produced by HakusuiTech Co., Ltd.", ultramarine blue that was "ultramarine produced by PINOA Co., Ltd.", iron oxide that was "a shika first-class product produced by KANTO CHEMICAL CO., INC.", and Red No. 204 that was "Lake Red CBA produced by Tokyo Chemical Industry Co., Ltd." were used.

Example 3

[Plasma Irradiation Treatment and/or Mechanical Energy Applying Treatment]

As a plasma irradiating device, the self-manufactured plasma generator was used. A 300 cc beaker was fixed on a slanted electric-powered turntable T-AU, rotated and used as a powder mixer used at the time of plasma irradiation.

The plasma generator is illustrated in FIGS. 1 and 2. In the Figures, the reference numeral 1 indicates AC/DC converter (AC 100 V→DC 24 V), the reference numeral 2 indicates a cold-cathode tube inverter (DC 24 V→AC 1000 V), the reference numeral 3 indicates a booster circuit (Cockcroft-Walton circuit, AC 1000 V→AC 10 kV), the reference numeral 4 indicates a plasma nozzle, and the reference numeral 5 indicates a gas flowmeter. Mechanofusion AMS-MINI (HOSOKAWA MICRON CORPORATION) was used as a device for applying mechanical energy, and a Nanocular NC-ALB (HOSOKAWA MICRON CORPORATION) was used as a device that enables application of mechanical energy and plasma irradiation simultaneously.

3-1 Production of Film-Forming Powders Provided with Plasma Irradiation Treatment The film-forming hydroxyapatite powders produced in Example 2-1, the film-forming hydroxyapatite powders in which silica was blended and that were produced in Example 2-2, and the film-forming hydroxyapatite powders in which color tone adjusters were blended and that were produced in Example 2-3 were provided with plasma irradiation treatment by using the self-manufactured plasma generator. Plasma irradiation treatment was performed with the film-forming powders mixed with the mixer (a 300 cc beaker was rotated by the electric-powered turntable T-AU) to obtain film-forming powders provided with plasma irradiation treatment.

3-2 Production of Film-Forming Hydroxyapatite Powders Provided with Plasma Irradiation Treatment and Mechanical Energy-Applying Treatment (Separate Treatments)

The film-forming hydroxyapatite powders produced in Example 2-1, the film-forming hydroxyapatite powders in which silica was blended and that were produced in Example 2-2, and the film-forming hydroxyapatite powders in which color tone adjusters were blended and that were produced in Example 2-3 were treated with a device for applying mechanical energy (Mechanofusion AMS-MINI, HOSOKAWA MICRON CORPORATION) and thereafter provided with plasma irradiation treatment to obtain film-forming powders. Similarly, the film-forming hydroxyapatite powder that was produced in Example 2-1 were treated with a device for applying mechanical energy after the treatment of plasma irradiation was performed to obtain a film-forming powder.

3-3 Production of Film-Forming Hydroxyapatite Powders Provided with Plasma Irradiation Treatment and Mechanical Energy-Applying Treatment (Simultaneous Treatments)

The film-forming hydroxyapatite powders produced in Example 2-1, the film-forming hydroxyapatite powders in which silica was blended and that were produced in Example 2-2, and the film-forming hydroxyapatite powders in which color tone adjusters were blended and that were produced in Example 2-3 were treated with the device that enables application of mechanical energy and plasma irradiation simultaneously (Nanocular NC-ALB, HOSOKAWA MICRON CORPORATION) to obtain film-forming powders.

3-4 Production of Film-Forming Hydroxyapatite Powders Provided with Mechanical Energy-Applying Treatment The film-forming hydroxyapatite powders produced in Example 2-1, the film-forming hydroxyapatite powders in which silica was blended and that were produced in Example 2-2, and the film-forming hydroxyapatite powders in which color tone adjusters were blended and that were produced in Example 2-3 were provided with the treatment of applying mechanical energy to obtain film-forming powders.

Example 4

[Measurement of Film Thickness, Elution Amount of Ca and Vickers Hardness]

Films were formed by the film-forming hydroxyapatite powders produced in Example 2-1, the film-forming hydroxyapatite powders in which silica was blended and that were produced in Example 2-2, and the film-forming hydroxyapatite powders in which color tone adjusters were blended and that were produced in Example 2-3. The measurements of the film thickness, the elution amount of Ca and the Vickers hardness were performed. Formed film layers containing the film-forming hydroxyapatite powders in which the above-mentioned color tone adjusters were blended (photographs) are illustrated in FIG. 6.

4-1 Particle Sizes of Film-Forming Powders

The mean particle sizes and the particle size distribution of the film-forming powders produced in Example 2-1 are illustrated in FIG. 3. A size distribution measuring device (LA-950, manufactured by HORIBA, Ltd.) was used for measuring the particle size distribution of the film-forming powders. The dry type unit was used for measurement. In [Tables] and the like described hereinafter, "a particle size of 0.5 μm" means a powder having a mean particle size of 0.4 to 0.6 μm, and "a particle size of 1 μm" means a powder having a mean particle size of 0.9 to 1.1 μm, "a particle size of 5 μm" means a powder having a mean particle size of 4.0 to 6.0 μm, "a particle size of 10 μm" means a powder having a mean particle size of 9.0 to 11.0 μm, "a particle size of 20 μm" means a powder having a mean particle size of 19.0 to 21.0 μm, and "a particle size of 30 μm" means a powder having a mean particle size of 29.0 to 31.0 μm.

4-2 Method for Forming Film

The enamel smooth surfaces were cut out of removed human teeth, and the surfaces were polished. Film formation treatment was performed on the above-mentioned polished surfaces by using the above-mentioned various hydroxyapatite film-forming powders by a device for forming a film by spraying a powder. As to film formation conditions, the inner diameter of handpiece tip nozzle was set as 5.0 mm, and the spray pressure was set as 0.6 MPa. The distance between a spray nozzle tip and a substrate was set as 0.5 cm (with the nozzle tip supported perpendicularly to a substrate), and the moving speed of the spray nozzle was set as 10 mm/s. The surface of the obtained formed film layers were polished with a diamond polisher paste. It was confirmed that the thicknesses of formed film layers did not change due to polishing treatment by using a digital microscope VHX-1000 (KEYENCE CORPORATION).

4-3 Measurement of Thicknesses of Formed Films

The thicknesses of the films formed by the film formation treatment of the above 4-2 were determined from results of the 3D measurement thereof by using the digital microscope VHX-1000 (KEYENCE CORPORATION).

4-4 Measurement of Elution Amounts of Ca from Films

All surfaces of samples other than surfaces on which the films were formed and on which the film formation treatment of the above-mentioned 4-2 was performed (windows of around 2 mm×2 mm) were masked with nail enamel to produce enamel blocks for measuring elution amounts of Ca. As to the evaluation of the elution amounts of Ca of the films, the concentrations of Ca ions eluted from formed film layers were measured by pH cycle tests in which the pH change in the oral cavity was simulated. A 0.2 mol/L lactic acid buffer solution (pH 4.5) and a 0.02 mol/L HEPES buffer solution (pH 7.0) were used for test solutions. The enamel blocks for measuring the Ca ion elution amounts, produced as described above were immersed in the lactic acid buffer solution under a 37° C. test condition for 30 minutes, and then, the enamel blocks were immersed in the HEPES buffer solution for 90 minutes. This was defined as one cycle. A total of 3 cycles were performed. After the end of tests, the concentration of Ca ions eluting in the solution was measured by ion chromatography (positive ion chromatography method). The measuring method was performed under the following measurement conditions:

Device name: Intelligent HPLC LC-2000-Plus (Jasco Corporation)
Measuring Column: Cation-Measuring Column IC YK-421 (Shodex)
Eluate: 5 mM tartaric acid+1 mM dipicolinic acid+1.5 g/L boric acid
Flow rate: 1.0 ml/min
Amount of charged sample: 20 μl
Column temperature: 40° C.
Detector: electrical conductivity detector.

4-5 Measurement of Vickers Hardness

The Vickers hardness of the films produced by film formation treatment was measured by using a micro hardness tester FM-700 (FUTURE-TECH CORP.) under the following conditions; pushing load: 100 g, and load retention time: 30 seconds.

Example 5

[Measurement Result 1]

Film formation treatment was performed by using the film-forming apatite powders produced in Example 2, and the measurements of the thicknesses of the formed films, elution amount of Ca, and Vickers hardness were performed on respective samples. A self-manufactured powder spraying device was used for forming films. The self-manufactured powder spraying device, comprise: an AC/DC converter (AC 100 V→DC 24 V), a solenoid valve, a mist separator, an air regulator, a speed controller, and the like.

5-1 Film Thicknesses

Film formation treatment was performed by using the film-forming apatite powders produced in Example 2-1, and the thicknesses of the formed films were measured. Measurement results of the thicknesses of the films formed by using the hydroxyapatite powders of various particle sizes that were calcined in the air atmosphere at 200 to 1350° C. are shown in [Table 1]. Measurement results of the thicknesses of the films formed by using the hydroxyapatite powders of various particle sizes that were calcined in an argon gas atmosphere at 600 to 1350° C. are shown in [Table 2]. Measurement results of the thicknesses of the films formed by using the hydroxyapatite powders of various particle sizes that were calcined in a nitrogen gas atmosphere at 600 to 1350° C. are shown in [Table 3]. And measurement results of the thicknesses of the films formed by using the fluorine apatite powders of various particle sizes that were calcined in the air atmosphere at 600 to 1350° C. are shown in [Table 4].

TABLE 1

Measurement of film thickness (μm)
Hydroxyapatite powder (calcined in the air atmosphere)

| Calcining temperature | Particle size | | | | | |
|---|---|---|---|---|---|---|
| | 0.5 μm | 1 μm | 5 μm | 10 μm | 20 μm | 30 μm |
| 200° C. | — | 2.2 | 1.7 | 2.1 | 2.5 | 2.8 |
| 400° C. | 4.3 | 9.9 | 11.3 | 11.7 | 12.9 | 13.9 |
| 600° C. | 26.9 | 34.4 | 35.2 | 37.4 | 33.8 | 31.3 |
| 800° C. | 53.2 | 71.4 | 71.9 | 72.2 | 68.3 | 63.2 |
| 1000° C. | 102.6 | 114.5 | 114.1 | 116.3 | 109.7 | 107.2 |
| 1100° C. | 103.0 | 114.2 | 114.6 | 117.4 | 109.4 | 108.6 |
| 1200° C. | 106.3 | 115.0 | 115.7 | 119.3 | 113.1 | 112.6 |
| 1300° C. | 106.1 | 114.7 | 118.4 | 119.7 | 113.5 | 112.3 |
| 1350° C. | 105.9 | 115.9 | 118.1 | 119.2 | 113.2 | 112.1 |

TABLE 2

Measurement of film thickness (μm)
Hydroxyapatite powder (calcined in an argon gas atmosphere)

| Calcining temperature | Particle size | | | | |
|---|---|---|---|---|---|
| | 0.5 μm | 1 μm | 5 μm | 10 μm | 30 μm |
| 600° C. | 32.1 | 36.7 | 37.4 | 39.1 | 33.2 |
| 1000° C. | 111.0 | 125.4 | 123.9 | 126.0 | 117.8 |
| 1200° C. | 116.3 | 128.7 | 129.3 | 131.3 | 120.6 |
| 1300° C. | 116.8 | 128.4 | 129.0 | 131.9 | 120.3 |
| 1350° C. | 115.7 | 127.5 | 128.2 | 130.2 | 119.1 |

TABLE 3

Measurement of film thickness (μm)
Hydroxyapatite powder (calcined in a nitrogen gas atmosphere)

| Calcining temperature | Particle size | | | | |
|---|---|---|---|---|---|
| | 0.5 μm | 1 μm | 5 μm | 10 μm | 30 μm |
| 600° C. | 30.6 | 35.8 | 36.6 | 38.7 | 32.4 |
| 1000° C. | 107.4 | 122.2 | 120.8 | 123.2 | 113.0 |
| 1200° C. | 110.2 | 123.1 | 124.3 | 127.8 | 118.9 |
| 1300° C. | 109.8 | 122.9 | 123.6 | 123.7 | 116.8 |
| 1350° C. | 109.0 | 121.3 | 122.1 | 123.6 | 117.1 |

TABLE 4

Measurement of film thickness (μm)
Fluorine apatite powder (calcined in the air atmosphere)

| Calcining temperature | Particle size | | | |
|---|---|---|---|---|
| | 0.5 μm | 1 μm | 10 μm | 30 μm |
| 600° C. | 27.2 | 32.1 | 35.8 | 31.5 |
| 1000° C. | 100.3 | 108.2 | 110.4 | 106.9 |
| 1200° C. | 104.4 | 113.4 | 116.3 | 111.7 |
| 1350° C. | 103.8 | 112.9 | 115.7 | 111.2 |

From the above results, although the film thicknesses in the case of forming films with a hydroxyapatite powder having a mean particle size of 0.5 μm and a fluorine apatite powders that were calcined in the air atmosphere at 600° C. were less than 30 μm, all the films formed with hydroxyapatite powders that were calcined in an argon gas atmosphere or a nitrogen gas atmosphere at 600 to 1350° C. and had a mean particle size of 0.5 to 30 μm had thicknesses of 30 μm or more. From this, it was revealed that superior thicknesses of films can be obtained when hydroxyapatite powders produced by calcining in an inert gas atmosphere, especially in an argon gas atmosphere, are used as film-forming powders.

5-2 Elution Amounts of Ca

Film formation treatment was performed by using the film-forming hydroxyapatite powders produced in Example 2-1, and the elution amounts of Ca were measured. Measurement results of elution amounts of Ca of the films formed by using the hydroxyapatite powders of various particle sizes that were calcined in the air atmosphere at 600 to 1350° C. are shown in [Table 5]. Measurement results of elution amounts of Ca of the films formed by using the hydroxyapatite powders of various particle sizes that were calcined in an argon gas atmosphere at 600 to 1350° C. are shown in [Table 6]. And measurement results of elution amounts of Ca of the films formed by using the hydroxyapatite powders of various particle sizes that were calcined in a nitrogen gas atmosphere at 600 to 1350° C. are shown in [Table 7].

TABLE 5

Measurement of elution amount (ppm) of Ca
Hydroxyapatite powder (calcined in the air atmosphere)

| Calcining temperature | Particle size | | | | |
|---|---|---|---|---|---|
| | 0.5 μm | 1 μm | 5 μm | 10 μm | 30 μm |
| 600° C. | 282 | 276 | 268 | 265 | 252 |
| 1000° C. | 184 | 171 | 166 | 163 | 165 |
| 1200° C. | 103 | 100 | 96 | 94 | 98 |
| 1350° C. | 108 | 106 | 105 | 103 | 101 |

TABLE 6

Measurement of elution amount (ppm) of Ca
Hydroxyapatite powder (calcined in an argon gas atmosphere)

| Calcining temperature | Particle size | | | | |
|---|---|---|---|---|---|
| | 0.5 μm | 1 μm | 5 μm | 10 μm | 30 μm |
| 600° C. | 231 | 227 | 214 | 212 | 204 |
| 1000° C. | 143 | 138 | 131 | 130 | 133 |

TABLE 6-continued

Measurement of elution amount (ppm) of Ca
Hydroxyapatite powder (calcined in an argon gas atmosphere)

| Calcining temperature | Particle size | | | | |
|---|---|---|---|---|---|
| | 0.5 μm | 1 μm | 5 μm | 10 μm | 30 μm |
| 1200° C. | 81 | 80 | 76 | 73 | 78 |
| 1350° C. | 87 | 84 | 81 | 80 | 80 |

TABLE 7

Measurement of elution amount (ppm) of Ca
Hydroxyapatite powder (calcined in a nitrogen gas atmosphere)

| Calcining temperature | Particle size | | | | |
|---|---|---|---|---|---|
| | 0.5 μm | 1 μm | 5 μm | 10 μm | 30 μm |
| 600° C. | 247 | 242 | 235 | 233 | 231 |
| 1000° C. | 161 | 149 | 144 | 141 | 144 |
| 1200° C. | 86 | 84 | 81 | 79 | 83 |
| 1350° C. | 91 | 89 | 87 | 85 | 86 |

From the above results, all the elution amounts of Ca in the case of forming films with hydroxyapatite powders that were calcined in an argon gas atmosphere or a nitrogen atmosphere at 600 to 1350° C. and had a mean particle size of 0.5 to 30 μm were reduced in comparison with the elution amounts of Ca in the case of forming films with hydroxyapatite powders that were calcined in the air atmosphere at 600 to 1350° C. and had a mean particle size of 0.5 to 30 μm. From this, it was revealed that the elution amount of Ca was suppressed by around 20% at the time when the hydroxyapatite powders produced by calcining in an inert gas atmosphere, especially in an argon gas atmosphere, are used as film-forming powders in comparison with the case when hydroxyapatite powders produced by calcining in the air atmosphere are used as film-forming powders.

5-3 Vickers Hardness

Film formation treatment was performed by using the film-forming hydroxyapatite powders produced in Example 2-1, and Vickers hardness was measured. Measurement results of Vickers hardness of the films formed by using the hydroxyapatite powders of various particle sizes that were calcined in the air atmosphere at 600 to 1350° C. are shown in [Table 8]. Measurement results of Vickers hardness of the films formed by using the hydroxyapatite powders of various particle sizes that were calcined in an argon gas atmosphere at 600 to 1350° C. are shown in [Table 9]. And measurement results of Vickers hardness of the films formed by using the hydroxyapatite powders of various particle sizes that were calcined in a nitrogen gas atmosphere at 600 to 1350° C. are shown in [Table 10].

TABLE 8

Measurement of Vickers hardness (Hv)
Hydroxyapatite powder (calcined in the air atmosphere)

| Calcining temperature | Particle size | | | | |
|---|---|---|---|---|---|
| | 0.5 μm | 1 μm | 5 μm | 10 μm | 30 μm |
| 600° C. | 302 | 304 | 306 | 305 | 307 |
| 1000° C. | 311 | 313 | 313 | 314 | 317 |
| 1200° C. | 320 | 324 | 327 | 328 | 326 |
| 1350° C. | 318 | 326 | 329 | 330 | 328 |

TABLE 9

Measurement of Vickers hardness (Hv)
Hydroxyapatite powder (calcined in an argon gas atmosphere)

| Calcining temperature | Particle size | | | | |
|---|---|---|---|---|---|
| | 0.5 μm | 1 μm | 5 μm | 10 μm | 30 μm |
| 600° C. | 351 | 353 | 357 | 356 | 354 |
| 1000° C. | 360 | 359 | 362 | 364 | 363 |
| 1200° C. | 382 | 384 | 390 | 388 | 385 |
| 1350° C. | 381 | 385 | 388 | 391 | 387 |

TABLE 10

Measurement of Vickers hardness (Hv)
Hydroxyapatite powder (calcined in a nitrogen gas atmosphere)

| Calcining temperature | Particle size | | | | |
|---|---|---|---|---|---|
| | 0.5 μm | 1 μm | 5 μm | 10 μm | 30 μm |
| 600° C. | 341 | 343 | 344 | 346 | 345 |
| 1000° C. | 352 | 356 | 355 | 356 | 359 |
| 1200° C. | 362 | 367 | 372 | 371 | 368 |
| 1350° C. | 357 | 368 | 371 | 373 | 369 |

From the above results, the Vickers hardness in the case of forming films with the hydroxyapatite powders that were calcined in the air atmosphere at 600 to 1350° C. and had a mean particle size of 0.5 to 30 μm was 302 to 330 Hv, and the Vickers hardness in all cases were 330 Hv or less. This numerical value was a value equivalent to a low level of the Vickers hardness of enamel reported by documents. Meanwhile, the Vickers hardness in the case of forming films with the hydroxyapatite powders that were calcined in an argon gas atmosphere at 600 to 1350° C. and had a mean particle size of 0.5 to 30 μm was 351 to 391 Hv, and the Vickers hardness in the case of forming films with the hydroxyapatite powders that were calcined in a nitrogen gas atmosphere at 600 to 1350° C. and had a mean particle size of 0.5 to 30 μm was 341 to 372 Hv. All the Vickers hardness was 340 Hv or more. These numerical values each indicated a value equivalent to a high level of the Vickers hardness of enamel reported by documents or a value exceeding the value and tended to become higher than that of natural dentine. From the above, it was revealed that the Vickers hardness in the case of using the hydroxyapatite powders produced by calcining in an inert gas atmosphere, especially in an argon gas atmosphere, are used as film-forming powders increased by around 15 to 18% in comparison with the Vickers hardness in the case of using the hydroxyapatite powders produced by calcining in the air atmosphere as film-forming powders.

From the above, in the hydroxyapatite powders calcined in an inert gas atmosphere, especially in an argon gas atmosphere, at 600 to 1350° C., the best results were obtained in all measurement results of the film thicknesses, the elution amounts of Ca, and the Vickers hardness of the films formed with the powders having a mean particle size of 0.5 to 30 μm, and it was revealed that the hydroxyapatite powders are effective powders as film-forming powders.

The Vickers hardness of the films that were formed with the hydroxyapatite powders calcined in the air atmosphere at 600 to 1350° C. was all 330 Hv or less. However, the Vickers hardness of the films that were formed with the hydroxyapatite powders calcined in an inert gas atmosphere at 600 to 1350° C. and having any particle size was recognized as a hardness of 340 Hv or more, and the hydroxyapatite powders were effective powders as film-forming powders.

Particularly, in the hydroxyapatite powders calcined in an argon gas atmosphere at 600 to 1350° C., the best results were obtained in all measurement results of the film thicknesses, the elution amounts of Ca and the Vickers hardness for the films formed with powders having a mean particle size of 0.5 to 30 μm.

5-4 Film Thickness (Having Color Tone Adjusters Blended)

Film formation treatment was performed by using film-forming hydroxyapatite powders having the color tone adjusters blended and which are produced in Example 2-3, and the thicknesses of the formed films were measured. Measurement results of the thicknesses of the films formed by using the hydroxyapatite powders of various particle sizes that were calcined in an argon gas atmosphere at 200 to 1350° C. and having 1% by mass of titanium oxide blended are shown in [Table 11]. And measurement results of the thicknesses of the films formed by using the hydroxyapatite powders of various particle sizes that were calcined in an argon gas atmosphere at 200 to 1350° C. and having 5% by mass of zinc oxide blended are shown in [Table 12].

TABLE 11

Measurement of film thickness (μm)
Film-forming powder in which color tone adjuster
is blended (1% of titanium oxide blended)

| Calcining temperature | Particle size | | | |
|---|---|---|---|---|
| | 0.5 μm | 1 μm | 10 μm | 30 μm |
| 200° C. | — | 2.9 | 2.7 | 2.6 |
| 400° C. | 6.2 | 12.5 | 12.1 | 11.9 |
| 600° C. | 32.7 | 36.3 | 34.7 | 33.6 |
| 1000° C. | 114.4 | 124.2 | 121.5 | 118.0 |
| 1200° C. | 125.8 | 128.1 | 125.4 | 121.3 |
| 1350° C. | 125.4 | 127.4 | 124.6 | 120.2 |

TABLE 12

Measurement of film thickness (μm)
Film-forming powder in which color tone adjuster
is blended (5% of zinc oxide blended)

| Calcining temperature | Particle size | | | |
|---|---|---|---|---|
| | 0.5 μm | 1 μm | 10 μm | 30 μm |
| 200° C. | — | 2.8 | 3.3 | 2.5 |
| 400° C. | 5.8 | 11.7 | 13.1 | 10.8 |
| 600° C. | 31.6 | 35.8 | 36.8 | 33.1 |
| 1000° C. | 111.0 | 121.5 | 124.7 | 117.4 |
| 1200° C. | 116.3 | 124.8 | 129.0 | 121.9 |
| 1350° C. | 115.8 | 124.4 | 127.9 | 120.6 |

From the above results, it was revealed that films that had high masking and hiding capability (film thickness: 30 μm or more) were formed in a short period of time with the powders that were calcined at 600 to 1350° C. in an argon gas atmosphere and had a mean particle size of 0.5 to 30 μm. When comparing the results shown in [Table 11] and [Table 12] with the results shown in [Table 2], it was revealed that the film thicknesses in the case of forming the films with the hydroxyapatite powders having 5% by mass of zinc oxide blended were nearly equivalent to the thicknesses in the case of blending no zinc oxide and the film thicknesses in the case of forming the films with the hydroxyapatite powders having 1% by mass of titanium oxide blended were rather superior to the thickness in the case of blending no titanium oxide.

Example 6

[Measurement Result 2]

Film formation treatments were performed with powders obtained by providing the film-forming apatite powders produced in Example 2 with mechanical energy-applying treatment followed by plasma irradiation treatment and untreated powders obtained by not providing the film-forming apatite powders with mechanical energy-applying treatment or plasma irradiation treatment, and the measurements of the film thicknesses, the elution amounts of Ca and the Vickers hardness were performed for respective samples. Similarly to Example 4-2, in film formation methods, enamel smooth surfaces were cut out of human removed teeth, and the surfaces were polished. Film formation treatments were performed on the above-mentioned polished surfaces by using various hydroxyapatite powders with the jet-device for forming a film by spraying a powder. Film formation conditions were set as follows: the inner diameter of a handpiece tip nozzle was 3.0 mm, the spray pressure was 0.4 MPa, the distance between a spray nozzle tip and a substrate was 10 mm (with the nozzle tip supported perpendicularly to a substrate), and the moving speed of the spray nozzle was 2 mm/s. The surfaces of the obtained formed film layers were polished with a diamond polisher paste.

6-1 Mechanical Energy-Applying Treatment Followed by Plasma Irradiation Treatment Mechanical energy-applying treatment was performed for 30 minutes with a rotor speed set as 500 rpm by using the device for applying mechanical energy (Mechanofusion AMS-MINI, Hosokawa Micron Corporation). Plasma treatment was performed for 5 minutes by irradiation with plasma under plasma generation conditions (an applied voltage of 20 kV) from a plasma nozzle tip with the container in which a powder provided with mechanical energy treatment was placed rotated at a rotor speed of 150 rpm. Helium, argon, nitrogen, carbonate or oxygen was used as a plasma gas.

(1) Hydroxyapatite Powder which was Calcined in Argon Gas Atmosphere and Having Particle Size of 1 μm The measurement results of the thicknesses of films formed with powders provided with mechanical energy-applying treatment to hydroxyapatite powders produced in Example 2-1 by calcining in an argon gas atmosphere at 600 to 1350° C. and had a particle size of 1 μm and thereafter irradiating the hydroxyapatite powder with plasma are shown in [Table 13], the measurement results of the elution amounts of Ca are shown in [Table 14], and the measurement results of the Vickers hardness thereof are shown in [Table 15]. All the results were classified by plasma gas types.

TABLE 13

Measurement of film thickness (μm)

| Calcining temperature | Mechanical energy → plasma treatment Gas type | | | | | Untreated |
|---|---|---|---|---|---|---|
| | He | Ar | $N_2$ | $CO_2$ | $O_2$ | — |
| 600° C. | 46.6 | 45.1 | 44.1 | 43.6 | 43.2 | 37.2 |
| 1000° C. | 161.2 | 157.5 | 154.7 | 154.1 | 151.9 | 122.1 |
| 1200° C. | 172.3 | 166.3 | 164.0 | 163.2 | 159.7 | 127.6 |
| 1350° C. | 171.9 | 165.4 | 163.6 | 162.4 | 159.1 | 126.4 |

TABLE 14

Measurement of elution amount (ppm) of Ca

| Calcining temperature | Mechanical energy → plasma treatment Gas type | | | | | Untreated |
|---|---|---|---|---|---|---|
| | He | Ar | $N_2$ | $CO_2$ | $O_2$ | — |
| 600° C. | 156 | 162 | 167 | 170 | 172 | 227 |
| 1000° C. | 67 | 86 | 92 | 96 | 101 | 138 |
| 1200° C. | 39 | 46 | 49 | 52 | 56 | 80 |
| 1350° C. | 41 | 50 | 52 | 56 | 60 | 84 |

TABLE 15

Measurement of Vickers hardness (Hv)

| Calcining temperature | Mechanical energy → plasma treatment Gas type | | | | | Untreated |
|---|---|---|---|---|---|---|
| | He | Ar | $N_2$ | $CO_2$ | $O_2$ | — |
| 600° C. | 426 | 423 | 419 | 413 | 411 | 355 |
| 1000° C. | 447 | 441 | 437 | 431 | 428 | 366 |
| 1200° C. | 483 | 477 | 472 | 465 | 460 | 387 |
| 1350° C. | 485 | 476 | 473 | 464 | 459 | 389 |

From the above results, the films formed with the powders provided with mechanical energy-applying treatment followed by plasma irradiation treatment were superior in all the items of the film thickness, the elution amount of Ca and the Vickers hardness as compared with the films formed with the untreated powders. The influence of plasma gas types was excellent in the following order: $He>Ar>N_2>CO_2>O_2$.

(2) Mixed Powder Obtained by Mixing Powder Calcined in Argon Gas Atmosphere with Powder Calcined in Air Atmosphere at Ratio 1 to 1

The measurement results of the film thicknesses of films formed with a mixed powder obtained by mixing a hydroxyapatite powder calcined in an argon gas atmosphere and having a particle size of 1 μm with a hydroxyapatite powder calcined in the air atmosphere and having a particle size of 1 μm at a ratio of 1 to 1, and performing mechanical energy-applying treatment followed by plasma irradiation treatment are shown in [Table 16]; the measurement results of the elution amounts of Ca are shown in [Table 17]; and the measurement results of Vickers hardness thereof are shown in [Table 18]. All the results were classified by plasma gas types.

TABLE 16

Measurement of film thickness (μm)

| Calcining temperature | Mechanical energy → plasma treatment Gas type | | | | | Untreated |
|---|---|---|---|---|---|---|
| | He | Ar | $N_2$ | $CO_2$ | $O_2$ | — |
| 600° C. | 35.7 | 35.6 | 35.4 | 35.2 | 35.3 | 34.9 |
| 1000° C. | 116.4 | 116.1 | 115.8 | 115.3 | 114.8 | 113.0 |
| 1200° C. | 121.2 | 120.8 | 120.4 | 120.3 | 120.1 | 117.3 |
| 1350° C. | 122.3 | 122.2 | 122.6 | 122.7 | 120.3 | 118.1 |

TABLE 17

Measurement of elution amount (ppm) of Ca

| Calcining temperature | Mechanical energy → plasma treatment Gas type | | | | | Untreated — |
|---|---|---|---|---|---|---|
| | He | Ar | N$_2$ | CO$_2$ | O$_2$ | |
| 600° C. | 196 | 205 | 213 | 208 | 221 | 234 |
| 1000° C. | 114 | 124 | 132 | 128 | 135 | 146 |
| 1200° C. | 65 | 68 | 72 | 70 | 74 | 81 |
| 1350° C. | 71 | 75 | 78 | 75 | 81 | 88 |

TABLE 18

Measurement of Vickers hardness (Hv)

| Calcining temperature | Mechanical energy → plasma treatment Gas type | | | | | Untreated — |
|---|---|---|---|---|---|---|
| | He | Ar | N$_2$ | CO$_2$ | O$_2$ | |
| 600° C. | 377 | 368 | 364 | 358 | 352 | 333 |
| 1000° C. | 396 | 387 | 382 | 376 | 371 | 347 |
| 1200° C. | 408 | 401 | 396 | 389 | 383 | 355 |
| 1350° C. | 409 | 399 | 395 | 390 | 384 | 354 |

From the above results, the films formed with the mixed powder provided with mechanical energy-applying treatment followed by plasma irradiation treatment were superior in all the items of the film thickness, the elution amount of Ca and the Vickers hardness to the films formed with the untreated powders. The influence of the plasma gas types was equivalent in the film thickness, excellent in the elution amount of Ca in the following order: He>Ar>CO$_2$>N$_2$>O$_2$, and excellent in the Vickers hardness in the following order: He>Ar>N$_2$>CO$_2$>O$_2$.

(3) Mixed Powder Obtained by Mixing Powder Calcined in Argon Gas Atmosphere and Powder Calcined in Nitrogen Gas Atmosphere at Ratio of 1 to 1

The measurement results of the film thicknesses of films formed with a mixed powder obtained by mixing a powder calcined in an argon gas atmosphere and having a particle size of 1 μm with a powder calcined in a nitrogen gas atmosphere and having a particle size of 1 μm at a ratio of 1 to 1, and performing mechanical energy-applying treatment followed by plasma irradiation treatment are shown in [Table 19]; the measurement results of the elution amounts of Ca are shown in [Table 20]; and the measurement results of Vickers hardness are shown in [Table 21]. All the results were classified by plasma gas types.

TABLE 19

Measurement of film thickness (μm)

| Calcining temperature | Mechanical energy → plasma treatment Gas type | | | | | Untreated — |
|---|---|---|---|---|---|---|
| | He | Ar | N$_2$ | CO$_2$ | O$_2$ | |
| 600° C. | 37.2 | 36.8 | 36.9 | 36.7 | 36.5 | 36.3 |
| 1000° C. | 122.1 | 121.5 | 120.8 | 120.5 | 120.2 | 118.5 |
| 1200° C. | 127.0 | 126.2 | 126.1 | 125.9 | 125.7 | 123.2 |
| 1350° C. | 127.6 | 127.3 | 126.8 | 126.4 | 126.4 | 123.7 |

TABLE 20

Measurement of elution amount (ppm) of Ca

| Calcining temperature | Mechanical energy → plasma treatment Gas type | | | | | Untreated — |
|---|---|---|---|---|---|---|
| | He | Ar | N$_2$ | CO$_2$ | O$_2$ | |
| 600° C. | 185 | 196 | 209 | 204 | 212 | 231 |
| 1000° C. | 101 | 115 | 125 | 121 | 128 | 144 |
| 1200° C. | 59 | 64 | 69 | 66 | 71 | 80 |
| 1350° C. | 64 | 68 | 72 | 69 | 75 | 83 |

TABLE 21

Measurement of Vickers hardness (Hv)

| Calcining temperature | Mechanical energy → plasma treatment Gas type | | | | | Untreated — |
|---|---|---|---|---|---|---|
| | He | Ar | N$_2$ | CO$_2$ | O$_2$ | |
| 600° C. | 411 | 404 | 400 | 395 | 393 | 347 |
| 1000° C. | 430 | 427 | 421 | 416 | 413 | 359 |
| 1200° C. | 458 | 454 | 449 | 445 | 442 | 381 |
| 1350° C. | 456 | 451 | 446 | 443 | 438 | 379 |

From the above results, the films formed with the mixed powder provided with mechanical energy-applying treatment followed by plasma irradiation treatment were superior in all the items of the film thickness, the elution amount of Ca and the Vickers hardness as compared with the films formed with the untreated powders. As for the influence of plasma gas types, He was excellent in the thickness, and in the elution amount of Ca the influence was excellent in the following order: He>Ar>CO$_2$>N$_2$>O$_2$, and in the Vickers hardness the influence was excellent in the following order: He>Ar>N$_2$>CO$_2$>O$_2$. The mixed powder obtained by mixing a powder calcined in an argon gas atmosphere with a powder calcined in a nitrogen gas atmosphere at a ratio of 1 to 1 was superior in all the items of the film thickness, the elution amount of Ca and the Vickers hardness as compared with the mixed powder obtained by mixing a powder calcined in an argon gas atmosphere with a powder calcined in the air atmosphere at a ratio of 1 to 1.

6-2 Mechanical Energy-Applying Treatment Followed by Plasma Irradiation Treatment (Blended with Color Tone Adjuster)

Films using powders obtained by providing film-forming hydroxyapatite powders which were produced in Example 2-3 and in which the color tone adjusters were blended with mechanical energy-applying treatment followed by plasma irradiation treatment, and using the untreated powders were formed. The film thicknesses, the elution amounts of Ca ions from the films and the Vickers hardness of the film were measured. Mechanical energy treatment was performed for 5 minutes with a rotor speed set as 5000 rpm by using a device for applying mechanical energy (Mechanofusion AMS-MINI, Hosokawa Micron Corporation). Plasma treatment was performed for 20 minutes by irradiation with plasma under plasma generation conditions (an applied voltage of 5 kV) from a plasma nozzle tip with the container in which the powder provided with mechanical energy treatment was placed rotated at a rotor speed of 150 rpm. Helium, argon, nitrogen, carbonate or oxygen was used as a plasma gas.

Similarly to the above-mentioned Example 4-2, in film formation methods, enamel smooth surfaces were cut out of human removed teeth, and the surfaces were polished. Film formation treatments were performed on the above-mentioned polished surfaces by using various hydroxyapatite powders with the device for forming a film by spraying a powder. Film formation conditions were set as follows: the inner diameter of a handpiece tip nozzle: 0.5 mm, the spray pressure: 0.2 MPa, the distance between a spray nozzle tip and a substrate: 30 mm (with the nozzle tip supported perpendicularly to a substrate), and the moving speed of the spray nozzle: 5 mm/s. The surface of the obtained formed film layers were polished with a diamond polisher paste.

The measurement results of the thicknesses of the films formed with powders provided with mechanical energy-applying treatment to the film-forming powders which were produced by calcining in an argon gas atmosphere and had a mean particle size of 1 μm and in which 1% by mass of titanium oxide was blended as a color tone adjuster, followed by plasma irradiation are shown in [Table 22]. The measurement results of the elution amounts of Ca are shown in [Table 23], and the measurement results of the Vickers hardness are shown in [Table 24]. All the results were classified by plasma gas types. Similarly, the measurement results of the thicknesses of films formed with powders provided with mechanical energy-applying treatment to film-forming powders obtained by blending 5% by mass of zinc oxide as a color tone adjuster into film-forming powders that were calcined in an argon gas atmosphere and had a mean particle size of 1 μm, followed by plasma irradiation are shown in [Table 25]. The measurement results of the elution amounts of Ca are shown in [Table 26], and the measurement results of the Vickers hardness thereof are shown in [Table 27]. All the results were classified by plasma gas types.

TABLE 22

Measurement of film thickness (μm)

| Calcining temperature | Mechanical energy → plasma treatment Gas type | | | | | Untreated — |
|---|---|---|---|---|---|---|
| | He | Ar | $N_2$ | $CO_2$ | $O_2$ | |
| 600° C. | 45.3 | 43.9 | 43.0 | 42.5 | 42.1 | 36.3 |
| 1000° C. | 165.3 | 159.6 | 157.3 | 156.0 | 154.4 | 124.2 |
| 1200° C. | 173.4 | 166.7 | 164.6 | 163.2 | 160.2 | 128.1 |
| 1350° C. | 171.5 | 166.1 | 164.1 | 162.8 | 159.5 | 127.4 |

TABLE 23

Measurement of elution amount (ppm) of Ca

| Calcining temperature | Mechanical energy → plasma treatment Gas type | | | | | Untreated — |
|---|---|---|---|---|---|---|
| | He | Ar | $N_2$ | $CO_2$ | $O_2$ | |
| 600° C. | 154 | 161 | 165 | 166 | 169 | 224 |
| 1000° C. | 67 | 87 | 93 | 96 | 101 | 139 |
| 1200° C. | 42 | 49 | 52 | 55 | 59 | 84 |
| 1350° C. | 45 | 55 | 57 | 61 | 65 | 91 |

TABLE 24

Measurement of Vickers hardness (Hv)

| Calcining temperature | Mechanical energy → plasma treatment Gas type | | | | | Untreated — |
|---|---|---|---|---|---|---|
| | He | Ar | $N_2$ | $CO_2$ | $O_2$ | |
| 600° C. | 425 | 421 | 416 | 412 | 409 | 354 |
| 1000° C. | 451 | 440 | 436 | 429 | 426 | 365 |
| 1200° C. | 483 | 477 | 472 | 464 | 461 | 387 |
| 1350° C. | 486 | 478 | 470 | 466 | 462 | 389 |

TABLE 25

Measurement of film thickness (μm)

| Calcining temperature | Mechanical energy → plasma treatment Gas type | | | | | Untreated — |
|---|---|---|---|---|---|---|
| | He | Ar | $N_2$ | $CO_2$ | $O_2$ | |
| 600° C. | 45.1 | 43.4 | 42.7 | 42.3 | 41.8 | 35.8 |
| 1000° C. | 161.4 | 156.6 | 154.2 | 153.1 | 151.4 | 121.5 |
| 1200° C. | 168.7 | 163.3 | 161.4 | 159.8 | 157.3 | 124.8 |
| 1350° C. | 168.2 | 162.8 | 160.8 | 159.5 | 156.7 | 124.4 |

TABLE 26

Measurement of elution amount (ppm) of Ca

| Calcining temperature | Mechanical energy → plasma treatment Gas type | | | | | Untreated — |
|---|---|---|---|---|---|---|
| | He | Ar | $N_2$ | $CO_2$ | $O_2$ | |
| 600° C. | 147 | 151 | 157 | 158 | 161 | 211 |
| 1000° C. | 62 | 78 | 84 | 86 | 91 | 124 |
| 1200° C. | 36 | 41 | 43 | 46 | 49 | 71 |
| 1350° C. | 39 | 44 | 46 | 49 | 52 | 75 |

TABLE 27

Measurement of Vickers hardness (Hv)

| Firing temperature | Mechanical energy → plasma treatment Gas type | | | | | Untreated — |
|---|---|---|---|---|---|---|
| | He | Ar | $N_2$ | $CO_2$ | $O_2$ | |
| 600° C. | 429 | 422 | 421 | 417 | 416 | 357 |
| 1000° C. | 447 | 443 | 441 | 440 | 439 | 368 |
| 1200° C. | 484 | 478 | 475 | 471 | 469 | 389 |
| 1350° C. | 489 | 476 | 478 | 473 | 470 | 392 |

From the above results, the films formed with the powders provided with mechanical energy-applying treatment followed by plasma irradiation treatment were superior in all the items of the film thickness, the elution amount of Ca and the Vickers hardness as compared with the films formed with the untreated powders. By using especially helium gas as a plasma gas, the speeds of forming film thicknesses were high, the elution amounts of Ca were suppressed, and high Vickers hardness was obtained also in Example 6-2 as in Example 6-1. Therefore, it was revealed that more densified and stable films can be formed.

From the above results, the films formed with the film-forming powders provided with mechanical energy treatment and plasma treatment, and the film-forming powders in which the color tone adjusters were blended exhibited a Vickers hardness of 380 Hv or more, and especially the films formed with the film-forming powders provided with plasma treatment after mechanical energy treatment all exhibited a value of 400 Hv or more. Therefore, it was found that the film-forming powders strengthen natural dentine. This becomes a great advantage for the purpose of extending the life of teeth. Since little difference between the film thicknesses formed with the film-forming powders in which the color tone adjusters were blended and that were provided with mechanical energy treatment and plasma treatment and the film thicknesses formed with the film-forming powders was found, it was revealed that color tone adjusters do not affect film formation.

Additionally, the elution amounts of Ca of the films formed with the film-forming powders provided with mechanical energy treatment and plasma treatment, and the film-forming powders in which the color tone adjusters were blended exhibited lower value than the elution amounts of Ca in the case of forming the films with the untreated (only mixed) film-forming powders and the film-forming powders provided with mechanical energy treatment, the stability of the formed films are improved, and dense films having high acid resistance can be obtained. Therefore, it is considered that films that stably exist in the oral cavity environment where the pH changes severely can be provided.

When the capability to hide the discoloration of a tooth crown was examined, it was revealed that it is preferable to form films having a film thickness of 30 μm or more. Therefore, a film-forming powder that enables forming film thicknesses of 30 μm or more in a short period of time and films having a Vickers hardness of 340 Hv or more, which is a medium level of the Vickers hardness of enamel, can be obtained.

Example 7

[Measurement Result 3]
[Difference of Effect Depending on Methods for Treating Powders Calcined in Different Atmospheres]
7-1 Experimental Conditions Films were formed by providing the following respective treatments to the film-forming apatite powders which were produced in Example 2: 1) the treatment of application of mechanical energy followed by plasma irradiation (mechanical energy→plasma treatment, separate treatments); 2) the treatment of plasma irradiation followed by application of mechanical energy (plasma treatment→mechanical energy, separate treatments); 3) the treatment of application of mechanical energy and plasma irradiation simultaneously (mechanical energy=plasma treatment, simultaneous treatments), 4) the treatment of plasma irradiation (plasma treatment); 5) the treatment of application of mechanical energy (mechanical energy treatment), and powders obtained 6) by only calcining, grinding, classifying and mixing with no treatment of plasma irradiation nor application of mechanical energy (untreated). The measurements of the film thickness, the elution amount of Ca and the Vickers hardness were performed for respective samples. The measurement of the film thicknesses, the elution amounts of Ca and the Vickers hardness was conducted in the same methods as Example 5.

Mechanical energy applying treatment was performed for 10 minutes with the rotor speed set as 2500 rpm by using the device for applying mechanical energy (Mechanofusion AMS-MINI, Hosokawa Micron Corporation). Plasma irradiation treatment was performed for 10 minutes by irradiation with plasma under plasma generation conditions (an applied voltage of 10 kV, plasma gas: helium) from a plasma nozzle tip with containers in which a powder not provided and provided with mechanical energy-applying treatment was placed rotated at a rotor speed of 150 rpm.

Similarly to Example 4-2, in film formation methods, enamel smooth surfaces were cut out of human removed teeth, and the surfaces were polished. Film formation treatments were performed on the above-mentioned polished surfaces by using various hydroxyapatite powders and hydroxyapatite powders having color tone adjusters blended with the device for forming a film by spraying a powder. Film formation conditions were set as follows: the inner diameter of a handpiece tip nozzle: 1.8 mm, the spray pressure: 0.5 MPa, the distance between a spray nozzle tip and a substrate: 5 mm (with the nozzle tip supported perpendicularly to a substrate), and the moving speed of the spray nozzle: 1 mm/s. The surface of the obtained formed film layers were polished with a diamond polisher paste.

7-2 Hydroxyapatite Powders Calcined in Argon Gas Atmosphere

Films were formed by using powders obtained by providing the above-mentioned 1) to 6) treatments to film-forming powders that were calcined in an argon atmosphere, ground and classified with the counter air flow mill. Results of the film thicknesses are shown in [Table 28] to [Table 30]. Results of the elution amount of Ca are shown in [Table 31] to [Table 33]. And results of the Vickers hardness are shown in [Table 34] to [Table 36].

TABLE 28

Measurement of film thickness (μm)

| | Mechanical energy → plasma treatment | | | | Mechanical energy + plasma treatment (simultaneous treatments) | | | |
|---|---|---|---|---|---|---|---|---|
| | Particle size | | | | | | | |
| Calcining temperature | 0.5 μm | 1 μm | 10 μm | 30 μm | 0.5 μm | 1 μm | 10 μm | 30 μm |
| 600° C. | 39.3 | 46.6 | 49.4 | 44.5 | 35.8 | 42.8 | 46.0 | 41.2 |
| 1000° C. | 145.6 | 161.2 | 164.1 | 160.8 | 134.3 | 150.1 | 152.2 | 148.6 |
| 1200° C. | 156.8 | 172.3 | 176.1 | 169.4 | 141.2 | 156.4 | 159.7 | 154.0 |
| 1350° C. | 156.4 | 171.9 | 175.6 | 168.8 | 140.7 | 155.6 | 159.3 | 154.3 |

TABLE 29

Measurement of film thickness (μm)

| | Plasma treatment → mechanical energy | | | | Untreated | | | |
|---|---|---|---|---|---|---|---|---|
| | Particle size | | | | | | | |
| Calcining temperature | 0.5 μm | 1 μm | 10 μm | 30 μm | 0.5 μm | 1 μm | 10 μm | 30 μm |
| 600° C. | 38.7 | 45.2 | 47.8 | 43.6 | 31.6 | 36.5 | 38.7 | 35.2 |
| 1000° C. | 143.3 | 158.5 | 159.1 | 157.2 | 110.9 | 121.8 | 122.4 | 121.1 |
| 1200° C. | 154.0 | 170.1 | 173.9 | 168.4 | 116.1 | 126.7 | 129.2 | 126.0 |
| 1350° C. | 154.5 | 169.6 | 173.4 | 168.1 | 115.8 | 126.3 | 128.9 | 126.3 |

TABLE 30

Measurement of film thickness (μm)

| Calcining temperature | Plasma treatment | | | | Mechanical energy treatment Particle size | | | | Untreated | | | |
|---|---|---|---|---|---|---|---|---|---|---|---|---|
| | 0.5 μm | 1 μm | 10 μm | 30 μm | 0.5 μm | 1 μm | 10 μm | 30 μm | 0.5 μm | 1 μm | 10 μm | 30 μm |
| 600° C. | 33.9 | 40.6 | 42.7 | 38.4 | 31.2 | 37.4 | 39.6 | 35.8 | 31.4 | 37.2 | 39.5 | 35.6 |
| 1000° C. | 125.8 | 140.2 | 140.1 | 136.8 | 110.5 | 122.4 | 123.9 | 121.1 | 110.3 | 122.1 | 123.9 | 121.3 |
| 1200° C. | 130.9 | 144.6 | 148.3 | 142.9 | 115.4 | 128.0 | 130.5 | 125.9 | 115.5 | 127.6 | 130.3 | 125.8 |
| 1350° C. | 129.6 | 144.9 | 148.5 | 142.7 | 115.7 | 126.9 | 129.7 | 126.4 | 115.3 | 126.4 | 129.8 | 126.2 |

TABLE 31

Measurement of elution amount (ppm) of Ca

| Calcining temperature | Mechanical energy → plasma treatment | | | | Mechanical energy + plasma treatment (simultaneous treatments) Particle size | | | |
|---|---|---|---|---|---|---|---|---|
| | 0.5 μm | 1 μm | 10 μm | 30 μm | 0.5 μm | 1 μm | 10 μm | 30 μm |
| 600° C. | 168 | 156 | 142 | 139 | 187 | 181 | 168 | 162 |
| 1000° C. | 72 | 67 | 63 | 67 | 111 | 108 | 102 | 105 |
| 1200° C. | 42 | 39 | 36 | 39 | 64 | 62 | 58 | 62 |
| 1350° C. | 45 | 41 | 39 | 41 | 69 | 66 | 63 | 64 |

TABLE 32

Measurement of elution amount (ppm) of Ca

| Calcining temperature | Plasma treatment → mechanical energy | | | | Untreated Particle size | | | |
|---|---|---|---|---|---|---|---|---|
| | 0.5 μm | 1 μm | 10 μm | 30 μm | 0.5 μm | 1 μm | 10 μm | 30 μm |
| 600° C. | 171 | 160 | 149 | 146 | 233 | 226 | 214 | 205 |
| 1000° C. | 74 | 68 | 67 | 68 | 144 | 136 | 133 | 131 |
| 1200° C. | 43 | 38 | 37 | 39 | 83 | 77 | 72 | 79 |
| 1350° C. | 44 | 39 | 40 | 40 | 87 | 80 | 78 | 80 |

TABLE 33

Measurement of elution amount (ppm) of Ca

| Calcining temperature | Plasma treatment | | | | Mechanical energy treatment Particle size | | | | Untreated | | | |
|---|---|---|---|---|---|---|---|---|---|---|---|---|
| | 0.5 μm | 1 μm | 10 μm | 30 μm | 0.5 μm | 1 μm | 10 μm | 30 μm | 0.5 μm | 1 μm | 10 μm | 30 μm |
| 600° C. | 207 | 204 | 188 | 183 | 228 | 231 | 210 | 203 | 231 | 227 | 212 | 204 |
| 1000° C. | 128 | 122 | 115 | 120 | 141 | 141 | 133 | 131 | 143 | 138 | 130 | 133 |
| 1200° C. | 72 | 70 | 64 | 68 | 82 | 79 | 72 | 78 | 81 | 80 | 73 | 78 |
| 1350° C. | 77 | 73 | 69 | 71 | 86 | 86 | 78 | 81 | 87 | 84 | 80 | 80 |

TABLE 34

Measurement of Vickers hardness (Hv)

| Calcining temperature | Mechanical energy → plasma treatment | | | | Mechanical energy + plasma treatment (simultaneous treatments) Particle size | | | |
|---|---|---|---|---|---|---|---|---|
| | 0.5 μm | 1 μm | 10 μm | 30 μm | 0.5 μm | 1 μm | 10 μm | 30 μm |
| 600° C. | 427 | 426 | 430 | 428 | 411 | 409 | 412 | 410 |
| 1000° C. | 443 | 447 | 446 | 445 | 423 | 425 | 428 | 426 |
| 1200° C. | 481 | 483 | 484 | 480 | 456 | 458 | 461 | 459 |
| 1350° C. | 479 | 485 | 487 | 482 | 454 | 457 | 460 | 461 |

TABLE 35

Measurement of Vickers hardness (Hv)

| Calcining temperature | Plasma treatment → mechanical energy | | | | Untreated Particle size | | | |
|---|---|---|---|---|---|---|---|---|
| | 0.5 μm | 1 μm | 10 μm | 30 μm | 0.5 μm | 1 μm | 10 μm | 30 μm |
| 600° C. | 423 | 427 | 430 | 424 | 351 | 356 | 357 | 354 |
| 1000° C. | 437 | 443 | 441 | 439 | 358 | 364 | 361 | 360 |
| 1200° C. | 470 | 472 | 474 | 476 | 379 | 381 | 379 | 382 |
| 1350° C. | 472 | 475 | 477 | 474 | 378 | 383 | 382 | 381 |

TABLE 36

Measurement of Vickers hardness (Hv)

| | Plasma treatment | | | | Mechanical energy treatment | | | | Untreated | | | |
|---|---|---|---|---|---|---|---|---|---|---|---|---|
| | Particle size | | | | | | | | | | | |
| Calcining temperature | 0.5 µm | 1 µm | 10 µm | 30 µm | 0.5 µm | 1 µm | 10 µm | 30 µm | 0.5 µm | 1 µm | 10 µm | 30 µm |
| 600° C. | 383 | 387 | 391 | 389 | 354 | 356 | 360 | 355 | 353 | 355 | 358 | 356 |
| 1000° C. | 399 | 404 | 402 | 404 | 358 | 368 | 363 | 368 | 361 | 366 | 364 | 367 |
| 1200° C. | 427 | 432 | 431 | 428 | 383 | 386 | 389 | 386 | 384 | 387 | 388 | 385 |
| 1350° C. | 424 | 433 | 430 | 426 | 385 | 391 | 391 | 387 | 382 | 389 | 390 | 388 |

From the above results, the films formed with 1) the powders that were provided with mechanical energy-applying treatment followed by plasma irradiation treatment; 2) the powders that were provided with mechanical energy-applying treatment after plasma irradiation treatment; 3) the powders that were provided with simultaneous mechanical energy-applying treatment and plasma irradiation treatment; and 4) the powders that were provided with plasma irradiation treatment were superior in all the items of the film thickness, the elution amount of Ca and the Vickers hardness regardless of the particle size than the films formed with 5) the powders that were provided with mechanical energy-applying treatment; and 6) the untreated powders nearly in the following order: 1)>2)>3)>4)>5)=6).

7-3 Film-Forming Apatite Powders

The same tests as the above 7-2 were also conducted for fluorine apatite, carbonate apatite, and magnesium-solid solution apatite that were synthesized in Example 2. Consequently, films formed by film-forming powders that were provided with the treatment of plasma irradiation (plasma treatment); and the treatments of both application of mechanical energy and plasma irradiation, especially the treatments of application of mechanical energy followed by plasma irradiation (mechanical energy→plasma treatment (separate treatments)), were superior in the film thickness, the elution amount of Ca and the Vickers hardness to films formed by using film-forming powders that were only calcined, ground, classified and mixed and that were provided with no treatment of plasma irradiation or application of mechanical energy (untreated). The same results as the cases of 7-2 were obtained.

7-4 Mixed Hydroxyapatite Powders Obtained by Mixing Hydroxyapatite Powders Calcined in Argon Gas Atmosphere and Hydroxyapatite Powders Calcined in Air Atmosphere at Ratio of 1 to 1

The same tests as the above 7-2 were conducted by using powders obtained by mixing hydroxyapatite powders calcined in an argon atmosphere, ground and classified with the counter air flow mill; and hydroxyapatite powders calcined in the air atmosphere, ground and classified with the counter air flow mill at a ratio of 1 to 1. Results of the film thicknesses are shown in [Table 37] and [Table 38]. Results of the elution amounts of Ca are shown in [Table 39] and [Table 40]. And results of the Vickers hardness are shown in [Table 41] and [Table 42].

TABLE 37

Measurement of film thickness (µm)

| | Mechanical energy → plasma treatment (separate treatments) | | | | Mechanical energy + plasma treatment (simultaneous treatments) | | | |
|---|---|---|---|---|---|---|---|---|
| | Particle size | | | | | | | |
| Calcining temperature | 0.5 µm | 1 µm | 10 µm | 30 µm | 0.5 µm | 1 µm | 10 µm | 30 µm |
| 600° C. | 33.1 | 40.8 | 43.5 | 39.3 | 31.2 | 38.3 | 40.9 | 36.5 |
| 1000° C. | 120.5 | 134.4 | 135.7 | 132.8 | 112.2 | 124.1 | 125.8 | 121.3 |
| 1200° C. | 126.3 | 140.2 | 144.1 | 137.7 | 116.0 | 129.3 | 132.5 | 127.0 |
| 1350° C. | 126.0 | 140.5 | 143.6 | 138.2 | 115.5 | 128.9 | 132.3 | 127.8 |

TABLE 38

Measurement of film thickness (µm)

| | Plasma treatment | | | | Mechanical energy treatment | | | | Untreated | | | |
|---|---|---|---|---|---|---|---|---|---|---|---|---|
| | Particle size | | | | | | | | | | | |
| Calcining temperature | 0.5 µm | 1 µm | 10 µm | 30 µm | 0.5 µm | 1 µm | 10 µm | 30 µm | 0.5 µm | 1 µm | 10 µm | 30 µm |
| 600° C. | 30.5 | 36.1 | 38.4 | 34.5 | 26.7 | 35.1 | 37.2 | 33.8 | 26.6 | 34.9 | 37.3 | 33.6 |
| 1000° C. | 105.1 | 115.3 | 117.2 | 114.8 | 101.5 | 113.3 | 115.2 | 112.4 | 101.3 | 113.0 | 114.8 | 112.2 |
| 1200° C. | 110.3 | 122.6 | 126.1 | 122.9 | 105.6 | 117.6 | 120.7 | 117.0 | 105.2 | 117.3 | 120.4 | 116.5 |
| 1350° C. | 109.6 | 123.4 | 125.8 | 123.3 | 105.2 | 118.5 | 119.9 | 117.4 | 104.8 | 118.1 | 119.5 | 117.2 |

TABLE 39

Measurement of elution amount (ppm) of Ca

| | Mechanical energy → plasma treatment (separate treatments) | | | | Mechanical energy + plasma treatment (simultaneous treatments) | | | |
|---|---|---|---|---|---|---|---|---|
| | Particle size | | | | | | | |
| Calcining temperature | 0.5 μm | 1 μm | 10 μm | 30 μm | 0.5 μm | 1 μm | 10 μm | 30 μm |
| 600° C. | 194 | 191 | 179 | 174 | 208 | 202 | 190 | 184 |
| 1000° C. | 103 | 98 | 92 | 95 | 129 | 124 | 118 | 120 |
| 1200° C. | 58 | 54 | 51 | 57 | 72 | 70 | 69 | 73 |
| 1350° C. | 63 | 59 | 58 | 59 | 77 | 77 | 75 | 76 |

TABLE 40

Measurement of elution amount (ppm) of Ca

| | Plasma treatment | | | | Mechanical energy treatment | | | | Untreated | | | |
|---|---|---|---|---|---|---|---|---|---|---|---|---|
| | Particle size | | | | | | | | | | | |
| Firing temperature | 0.5 μm | 1 μm | 10 μm | 30 μm | 0.5 μm | 1 μm | 10 μm | 30 μm | 0.5 μm | 1 μm | 10 μm | 30 μm |
| 600° C. | 228 | 221 | 207 | 199 | 237 | 237 | 221 | 210 | 239 | 234 | 219 | 211 |
| 1000° C. | 141 | 136 | 128 | 130 | 153 | 144 | 136 | 143 | 151 | 146 | 137 | 140 |
| 1200° C. | 78 | 76 | 74 | 79 | 84 | 83 | 80 | 87 | 84 | 81 | 79 | 84 |
| 1350° C. | 85 | 82 | 78 | 80 | 90 | 88 | 84 | 86 | 91 | 88 | 86 | 86 |

TABLE 41

Measurement of Vickers hardness (Hv)

| | Mechanical energy → plasma treatment (separate treatments) | | | | Mechanical energy + plasma treatment (simultaneous treatments) | | | |
|---|---|---|---|---|---|---|---|---|
| | Particle size | | | | | | | |
| Calcining temperature | 0.5 μm | 1 μm | 10 μm | 30 μm | 0.5 μm | 1 μm | 10 μm | 30 μm |
| 600° C. | 373 | 377 | 376 | 380 | 344 | 349 | 346 | 351 |
| 1000° C. | 391 | 396 | 395 | 398 | 361 | 369 | 367 | 371 |
| 1200° C. | 404 | 408 | 411 | 412 | 377 | 381 | 382 | 384 |
| 1350° C. | 402 | 409 | 413 | 410 | 373 | 382 | 384 | 383 |

TABLE 42

Measurement of Vickers hardness (Hv)

| | Plasma treatment | | | | Mechanical energy treatment | | | | Untreated | | | |
|---|---|---|---|---|---|---|---|---|---|---|---|---|
| | Particle size | | | | | | | | | | | |
| Calcining temperature | 0.5 μm | 1 μm | 10 μm | 30 μm | 0.5 μm | 1 μm | 10 μm | 30 μm | 0.5 μm | 1 μm | 10 μm | 30 μm |
| 600° C. | 336 | 340 | 339 | 342 | 329 | 334 | 329 | 333 | 329 | 333 | 331 | 335 |
| 1000° C. | 352 | 358 | 356 | 359 | 341 | 346 | 347 | 350 | 342 | 347 | 346 | 349 |
| 1200° C. | 365 | 370 | 372 | 372 | 353 | 356 | 355 | 358 | 351 | 355 | 357 | 358 |
| 1350° C. | 363 | 371 | 370 | 373 | 349 | 355 | 358 | 358 | 348 | 354 | 359 | 356 |

From the above results, the films formed with 1) the powders that were provided with mechanical energy-applying treatment followed by plasma irradiation treatment; 3) the powders that were provided with simultaneous mechanical energy-applying treatment and plasma irradiation treatment; and 4) the powders that were provided with plasma irradiation treatment were superior in all the items of the film thickness, the elution amount of Ca and the Vickers hardness regardless of the particle size as compared with the films formed with 5) the powders that were provided with mechanical energy-applying treatment; and 6) the untreated powders nearly in the following order: 1)>3)>4)>5)=6). In the powders obtained by mixing the film-forming powders calcined in an argon gas atmosphere, which was an inert gas, and the hydroxyapatite powders calcined in the air atmosphere at a ratio of 1 to 1, it was found that the film thicknesses of the formed films were 30 μm or more when the powders were provided with the treatment of plasma irradiation (plasma treatment); and the treatment of both application of mechanical energy and plasma irradiation, and it was revealed that the powders serve as effective film-forming powders. Films formed with hydroxyapatite powders obtained by mixing the hydroxyapatite powders calcined in an argon gas atmosphere and the hydroxyapatite powders calcined in the air atmosphere at a ratio of 1 to 1 were inferior to films formed with hydroxyapatite powders calcined in an argon gas atmosphere in all the items of the film thickness, the elution amount of Ca and the Vickers hardness.

7-5 Mixed Hydroxyapatite Powders Obtained by Mixing Hydroxyapatite Powders Calcined in Argon Gas Atmosphere and Hydroxyapatite Powders Calcined in Nitrogen Atmosphere at Ratio of 1 to 1

The same tests as the above 7-2 were conducted by using powders obtained by mixing hydroxyapatite powders calcined in an argon atmosphere, ground and classified with the counter air flow mill; and hydroxyapatite powders calcined in a nitrogen atmosphere, ground and classified with the counter air flow mill at a ratio of 1 to 1. Results of the film thicknesses are shown in [Table 43] and [Table 44]. Results of the elution amounts of Ca are shown in [Table 45] and [Table 46]. And results of the Vickers hardness are shown in [Table 47] and [Table 48].

TABLE 43

Measurement of film thickness (μm)

| Calcining temperature | Mechanical energy → plasma treatment (separate treatments) | | | | Mechanical energy + plasma treatment (simultaneous treatments) | | | |
|---|---|---|---|---|---|---|---|---|
| | Particle size | | | | | | | |
| | 0.5 μm | 1 μm | 10 μm | 30 μm | 0.5 μm | 1 μm | 10 μm | 30 μm |
| 600° C. | 36.4 | 43.8 | 47.1 | 42.3 | 33.9 | 41.1 | 43.6 | 39.2 |
| 1000° C. | 133.5 | 149.4 | 150.9 | 149.0 | 124.8 | 140.2 | 141.3 | 137.9 |
| 1200° C. | 142.3 | 157.7 | 161.2 | 157.4 | 131.1 | 146.1 | 149.2 | 144.4 |
| 1350° C. | 142.0 | 158.2 | 160.6 | 157.9 | 130.9 | 146.5 | 148.4 | 145.3 |

TABLE 44

Measurement of film thickness (μm)

| Calcining temperature | Plasma treatment | | | | Mechanical energy treatment | | | | Untreated | | | |
|---|---|---|---|---|---|---|---|---|---|---|---|---|
| | Particle size | | | | | | | | | | | |
| | 0.5 μm | 1 μm | 10 μm | 30 μm | 0.5 μm | 1 μm | 10 μm | 30 μm | 0.5 μm | 1 μm | 10 μm | 30 μm |
| 600° C. | 31.6 | 38.2 | 40.5 | 36.8 | 30.3 | 36.6 | 38.6 | 34.9 | 30.2 | 36.3 | 38.5 | 34.7 |
| 1000° C. | 113.5 | 128.3 | 129.6 | 127.9 | 105.7 | 118.8 | 119.7 | 118.0 | 105.5 | 118.5 | 119.4 | 117.8 |
| 1200° C. | 120.7 | 136.1 | 138.4 | 135.2 | 110.3 | 123.5 | 126.4 | 123.3 | 110.6 | 123.2 | 126.1 | 122.9 |
| 1350° C. | 120.4 | 136.8 | 138.3 | 135.5 | 110.2 | 123.6 | 127.9 | 123.6 | 110.2 | 123.7 | 125.3 | 124.0 |

TABLE 45

Measurement of elution amount (ppm) of Ca

| Calcining temperature | Mechanical energy → plasma treatment (separate treatments) | | | | Mechanical energy + plasma treatment (simultaneous treatments) | | | |
|---|---|---|---|---|---|---|---|---|
| | Particle size | | | | | | | |
| | 0.5 μm | 1 μm | 10 μm | 30 μm | 0.5 μm | 1 μm | 10 μm | 30 μm |
| 600° C. | 183 | 175 | 163 | 150 | 198 | 194 | 181 | 172 |
| 1000° C. | 86 | 79 | 74 | 75 | 119 | 116 | 109 | 111 |
| 1200° C. | 49 | 44 | 42 | 46 | 68 | 65 | 63 | 68 |
| 1350° C. | 52 | 48 | 47 | 48 | 72 | 70 | 68 | 70 |

TABLE 46

Measurement of elution amount (ppm) of Ca

| Calcining temperature | Plasma treatment | | | | Mechanical energy treatment | | | | Untreated | | | |
|---|---|---|---|---|---|---|---|---|---|---|---|---|
| | Particle size | | | | | | | | | | | |
| | 0.5 μm | 1 μm | 10 μm | 30 μm | 0.5 μm | 1 μm | 10 μm | 30 μm | 0.5 μm | 1 μm | 10 μm | 30 μm |
| 600° C. | 214 | 210 | 196 | 188 | 235 | 234 | 217 | 207 | 237 | 231 | 216 | 207 |
| 1000° C. | 133 | 129 | 124 | 123 | 148 | 142 | 137 | 136 | 149 | 144 | 135 | 136 |
| 1200° C. | 76 | 72 | 70 | 74 | 83 | 80 | 75 | 81 | 84 | 80 | 77 | 83 |
| 1350° C. | 80 | 78 | 76 | 76 | 91 | 84 | 83 | 84 | 89 | 86 | 84 | 84 |

TABLE 47

Measurement of Vickers hardness (Hv)

| Calcining temperature | Mechanical energy → plasma treatment (separate treatments) | | | | Mechanical energy + plasma treatment (simultaneous treatments) | | | |
|---|---|---|---|---|---|---|---|---|
| | Particle size | | | | | | | |
| | 0.5 μm | 1 μm | 10 μm | 30 μm | 0.5 μm | 1 μm | 10 μm | 30 μm |
| 600° C. | 407 | 411 | 409 | 413 | 385 | 390 | 387 | 392 |
| 1000° C. | 426 | 430 | 427 | 431 | 405 | 411 | 408 | 411 |
| 1200° C. | 451 | 458 | 456 | 454 | 430 | 439 | 436 | 434 |
| 1350° C. | 448 | 456 | 457 | 453 | 427 | 436 | 438 | 435 |

TABLE 48

Measurement of Vickers hardness (Hv)

| Calcining temperature | Plasma treatment | | | | Mechanical energy treatment | | | | Untreated | | | |
|---|---|---|---|---|---|---|---|---|---|---|---|---|
| | Particle size | | | | | | | | | | | |
| | 0.5 μm | 1 μm | 10 μm | 30 μm | 0.5 μm | 1 μm | 10 μm | 30 μm | 0.5 μm | 1 μm | 10 μm | 30 μm |
| 600° C. | 359 | 364 | 362 | 365 | 343 | 344 | 346 | 348 | 342 | 347 | 345 | 349 |
| 1000° C. | 378 | 383 | 381 | 384 | 351 | 361 | 357 | 358 | 353 | 359 | 356 | 358 |
| 1200° C. | 402 | 411 | 409 | 406 | 374 | 382 | 378 | 374 | 372 | 381 | 379 | 376 |
| 1350° C. | 399 | 410 | 413 | 408 | 369 | 377 | 382 | 376 | 370 | 379 | 382 | 377 |

From the above results, the films formed with 1) the powders that were provided with mechanical energy-applying treatment followed by plasma irradiation treatment; 3) the powders that were provided with simultaneous mechanical energy-applying treatment and plasma irradiation treatment; and 4) the powders that were provided with plasma irradiation treatment were superior in all the items of the film thickness, the elution amount of Ca and the Vickers hardness regardless of the particle size as compared with the films formed with 5) the powders that were provided with mechanical energy-applying treatment; and 6) the untreated powders nearly in the following order: 1)>3)>4)>5)=6). The films formed with the hydroxyapatite powders obtained by mixing the hydroxyapatite powders calcined in an argon gas atmosphere and the hydroxyapatite powders calcined in a nitrogen atmosphere at a ratio of 1 to 1 were superior as compared with the films formed with the hydroxyapatite powders obtained by mixing the hydroxyapatite powders calcined in an argon gas atmosphere and the hydroxyapatite powders calcined in the air atmosphere at a ratio of 1 to 1 in all the items of the film thickness, the elution amount of Ca and the Vickers hardness, but were inferior to the films formed with the hydroxyapatite powders calcined in an argon gas atmosphere in all the items of the film thickness, the elution amount of Ca and the Vickers hardness.

7-6 Film-Forming Hydroxyapatite Powders Blended with Silica

The same tests as the above 7-2 were conducted by using the film-forming powder having a particle size of 1 μm to which silica was added that was obtained by calcining the powder obtained by adding 1% of the silica powder to the hydroxyapatite powders having a mean particle size of 1 μm in an argon atmosphere, grinding and classifying the powder with the counter air flow mill as described in the above-mentioned Example 2-2. Results of the film thicknesses are shown in [Table 49] and [Table 50]. Results of the elution amounts of Ca are shown in [Table 51] and [Table 52]. And results of the Vickers hardness are shown in [Table 53] and [Table 54].

TABLE 49

Measurement of film thickness (μm)

| Calcining temperature | Mechanical energy → plasma treatment (separate treatments) | Mechanical energy + plasma treatment (simultaneous treatments) |
|---|---|---|
| | Particle size | |
| | 1 μm | 1 μm |
| 600° C. | 42.8 | 39.4 |
| 1000° C. | 153.6 | 142.6 |
| 1200° C. | 162.6 | 148.5 |
| 1350° C. | 162.5 | 148.2 |

TABLE 50

Measurement of film thickness (μm)

| Calcining temperature | Plasma treatment | Mechanical energy treatment | Untreated |
|---|---|---|---|
| | Particle size | | |
| | 1 μm | 1 μm | 1 μm |
| 600° C. | 36.1 | 34.3 | 34.5 |
| 1000° C. | 131.4 | 116.9 | 116.7 |
| 1200° C. | 138.6 | 121.8 | 121.3 |
| 1350° C. | 137.9 | 121.4 | 121.1 |

TABLE 51

Measurement of elution amount (ppm) of Ca

| Calcining temperature | Mechanical energy → plasma treatment (separate treatments) | Mechanical energy + plasma treatment (simultaneous treatments) |
|---|---|---|
| | Particle size | |
| | 1 μm | 1 μm |
| 600° C. | 161 | 184 |
| 1000° C. | 70 | 108 |
| 1200° C. | 41 | 63 |
| 1350° C. | 44 | 67 |

TABLE 52

Measurement of elution amount (ppm) of Ca

| Calcining temperature | Plasma treatment Particle size 1 μm | Mechanical energy treatment 1 μm | Untreated 1 μm |
|---|---|---|---|
| 600° C. | 204 | 225 | 227 |
| 1000° C. | 121 | 135 | 136 |
| 1200° C. | 68 | 77 | 78 |
| 1350° C. | 74 | 85 | 84 |

TABLE 53

Measurement of Vickers hardness (Hv)

| Calcining temperature | Mechanical energy → plasma treatment (separate treatments) Particle size 1 μm | Mechanical energy + plasma treatment (simultaneous treatments) 1 μm |
|---|---|---|
| 600° C. | 427 | 411 |
| 1000° C. | 449 | 429 |
| 1200° C. | 482 | 465 |
| 1350° C. | 486 | 467 |

TABLE 54

Measurement of Vickers hardness (Hv)

| Calcining temperature | Plasma treatment Particle size 1 μm | Mechanical energy treatment 1 μm | Untreated 1 μm |
|---|---|---|---|
| 600° C. | 382 | 356 | 358 |
| 1000° C. | 399 | 370 | 370 |
| 1200° C. | 426 | 392 | 391 |
| 1350° C. | 429 | 394 | 393 |

From the above results, the films formed with 1) the powders that were provided with mechanical energy-applying treatment followed by plasma irradiation treatment; 3) the powders that were provided with simultaneous mechanical energy-applying treatment and plasma irradiation treatment; and 4) the powders that were provided with plasma irradiation treatment were superior in all the items of the film thickness, the elution amount of Ca and the Vickers hardness regardless of the calcining temperature as compared with the films formed with 5) the powders that were provided with mechanical energy-applying treatment; and 6) the untreated powders nearly in the following order: 1)>3)>4)>5)=6). The films formed with the film-forming hydroxyapatite powder having silica blended were a little inferior to the films formed with the hydroxyapatite powder in which silica was not blended and that was calcined in an argon gas atmosphere in the film thickness, but were as excellent as the films formed with the hydroxyapatite powder in which silica was not blended and that was calcined in an argon gas atmosphere in the elution amount of Ca and the Vickers hardness.

7-7 Mixed Powder Obtained by Mixing Hydroxyapatite Powders Different in Particle Size The same tests as the above 7-2 were conducted by using powders obtained by mixing film-forming hydroxyapatite powders which were calcined in an argon atmosphere, ground and classified with the counter air flow mill and had a mean particle size of 10 μm; and film-forming hydroxyapatite powders which were calcined in an argon atmosphere, ground and classified with the counter air flow mill and had a mean particle size of 1 μm, at a ratio of 1 to 1. Results of the film thicknesses are shown in [Table 55] and [Table 56]. Results of the film thicknesses for comparison are shown in [Table 57]. Results of the elution amounts of Ca are shown in [Table 58] and [Table 59]. Results of the elution amounts of Ca for comparison are shown in [Table 60]. Results of the Vickers hardness are shown in [Table 61] and [Table 62]. Results of the Vickers hardness for comparison are shown in [Table 63].

TABLE 55

Measurement of film thickness (μm)

| Calcining temperature | Mechanical energy → plasma treatment (separate treatments) Particle size 10 μm + 1 μm | Mechanical energy + plasma treatment (simultaneous treatments) 10 μm + 1 μm |
|---|---|---|
| 600° C. | 52.3 | 47.1 |
| 1000° C. | 175.2 | 157.6 |
| 1200° C. | 189.6 | 165.4 |
| 1350° C. | 189.2 | 165.0 |

TABLE 56

Measurement of film thickness (μm)

| Calcining temperature | Plasma treatment Particle size 10 μm + 1 μm | Mechanical energy treatment 10 μm + 1 μm | Untreated 10 μm + 1 μm |
|---|---|---|---|
| 600° C. | 43.3 | 39.6 | 39.7 |
| 1000° C. | 139.0 | 124.1 | 123.8 |
| 1200° C. | 147.8 | 131.0 | 130.6 |
| 1350° C. | 147.3 | 129.5 | 129.9 |

TABLE 57

Measurement of film thickness (μm)

| Calcining temperature | Mechanical energy → plasma treatment (separate treatments) Particle size 1 μm | 10 μm |
|---|---|---|
| 600° C. | 46.6 | 49.4 |
| 1000° C. | 161.2 | 164.1 |
| 1200° C. | 172.3 | 176.1 |
| 1350° C. | 171.9 | 175.6 |

TABLE 58

Measurement of elution amount (ppm) of Ca

| Calcining temperature | Mechanical energy → plasma treatment (separate treatments) Particle size 10 μm + 1 μm | Mechanical energy + plasma treatment (simultaneous treatments) Particle size 10 μm + 1 μm |
|---|---|---|
| 600° C. | 131 | 159 |
| 1000° C. | 57 | 97 |
| 1200° C. | 32 | 55 |
| 1350° C. | 35 | 60 |

TABLE 59

Measurement of elution amount (ppm) of Ca

| Calcining temperature | Plasma treatment Particle size 10 μm + 1 μm | Mechanical energy treatment 10 μm + 1 μm | Untreated 10 μm + 1 μm |
|---|---|---|---|
| 600° C. | 184 | 203 | 207 |
| 1000° C. | 112 | 125 | 127 |
| 1200° C. | 62 | 74 | 72 |
| 1350° C. | 68 | 77 | 78 |

TABLE 60

Measurement of elution amount (ppm) of Ca

| Calcining temperature | Mechanical energy → plasma treatment (separate treatments) Particle size 1 μm | 10 μm |
|---|---|---|
| 600° C. | 156 | 142 |
| 1000° C. | 67 | 63 |
| 1200° C. | 39 | 36 |
| 1350° C. | 41 | 39 |

TABLE 61

Measurement of Vickers hardness (Hv)

| Calcining temperature | Mechanical energy → plasma treatment (separate treatments) Particle size 10 μm + 1 μm | Mechanical energy + plasma treatment (simultaneous treatments) Particle size 10 μm + 1 μm |
|---|---|---|
| 600° C. | 438 | 419 |
| 1000° C. | 457 | 436 |
| 1200° C. | 499 | 473 |
| 1350° C. | 497 | 470 |

TABLE 62

Measurement of Vickers hardness (Hv)

| Calcining temperature | Plasma treatment 10 μm + 1 μm | Mechanical energy treatment Particle size 10 μm + 1 μm | Untreated 10 μm + 1 μm |
|---|---|---|---|
| 600° C. | 397 | 362 | 361 |
| 1000° C. | 408 | 366 | 369 |
| 1200° C. | 439 | 397 | 392 |
| 1350° C. | 438 | 396 | 393 |

TABLE 63

Measurement of Vickers hardness (Hv)

| Calcining temperature | Mechanical energy → plasma treatment (separate treatments) Particle size 1 μm | 10 μm |
|---|---|---|
| 600° C. | 426 | 430 |
| 1000° C. | 447 | 446 |
| 1200° C. | 483 | 484 |
| 1350° C. | 485 | 487 |

From the above results, the films formed with 1) the powders that were provided with mechanical energy-applying treatment followed by plasma irradiation treatment; 3) the powders that were provided with simultaneous mechanical energy-applying treatment and plasma irradiation treatment; and 4) the powders that were provided with plasma irradiation treatment were superior in all the items of the film thickness, the elution amount of Ca and the Vickers hardness regardless of the calcining temperature to the films formed with 5) the powders that were provided with mechanical energy-applying treatment; and 6) the untreated powders nearly in the following order: 1)>3)>4)>5)=6). The films formed with the powders obtained by using the hydroxyapatite powders obtained by mixing the film-forming hydroxyapatite powders having a mean particle size of 1 μm and the film-forming hydroxyapatite powders having a mean particle size of 10 μm at a ratio of 1 to 1 and performing mechanical energy-applying treatment followed by plasma irradiation treatment were superior in all the items of the thickness of a formed film, the elution amount of Ca, and the Vickers hardness to the films formed with the powders obtained by using the film-forming hydroxyapatite powders having a mean particle size of 1 μm and the film-forming hydroxyapatite powders having a mean particle size of 10 μm and performing mechanical energy-applying treatment followed by plasma irradiation treatment.

As understood from the above experimental results, film-forming powders preferable for forming films having a high hardness and low solubility in acid (films having a small elution amount of Ca) in a short period of time were obtained by performing the treatment of plasma irradiation (plasma treatment). Film-forming powders preferable for forming films having higher hardness and extremely low solubility in acid for a shorter period of time were obtained especially by performing the treatments of application of mechanical energy followed by plasma irradiation (mechanical energy→plasma treatment, separate treatments).

Example 8

[Film-Forming Hydroxyapatite Powders Having Color Tone Adjusters Blended]

Films were formed by providing the following respective treatments to powders obtained by blending color tone adjusters in the film-forming powders that were calcined in an argon atmosphere, ground and classified with the counter air flow mill as described in the Example 2-3: 1) the treatments of application of mechanical energy followed by plasma irradiation (mechanical energy→plasma treatment, separate treatments); 3) the treatment of application of mechanical energy and plasma irradiation simultaneously (mechanical energy=plasma treatment, simultaneous treatments), 4) the treatment of plasma irradiation (plasma treatment); 5) the treatment of application of mechanical energy (mechanical energy treatment), and powders obtained 6) by only calcining, grinding, classifying and mixing with no treatment of application of mechanical energy nor plasma irradiation (untreated). The measurements of the film thickness, the elution amount of Ca and the Vickers hardness were performed for respective samples similarly as in Example 7. The measuring methods of the film thicknesses, the elution amounts of Ca and the Vickers hardness were performed by the same methods as in Example 5.

8-1 Powders in which 1% by Mass of Titanium Oxide was Blended as Color Tone Adjuster Films were formed by using the powders obtained by providing the above-mentioned treatments of 1) and 3) to 6) to the powders obtained by blending 1% by mass of titanium oxide as a color tone adjuster in the film-forming powders that were calcined in an argon atmosphere, ground and classified with the counter air flow mill. Results of the film thicknesses are shown in [Table 64] and [Table 65]. Results of the elution amounts of Ca are shown in [Table 66] and [Table 67]. And results of Vickers hardness are shown in [Table 68] and [Table 69].

TABLE 64

Measurement of film thickness (μm)

| | Mechanical energy → plasma treatment (separate treatments) | | | | Mechanical energy + plasma treatment (simultaneous treatments) | | | |
|---|---|---|---|---|---|---|---|---|
| | Particle size | | | | | | | |
| Calcining temperature | 0.5 μm | 1 μm | 10 μm | 30 μm | 0.5 μm | 1 μm | 10 μm | 30 μm |
| 600° C. | 40.1 | 45.3 | 43.7 | 42.2 | 37.3 | 41.7 | 40.2 | 38.8 |
| 1000° C. | 154.4 | 165.3 | 162.1 | 157.9 | 139.7 | 152.4 | 148.2 | 143.9 |
| 1200° C. | 170.2 | 173.4 | 169.6 | 165.0 | 152.5 | 157.0 | 154.6 | 149.4 |
| 1350° C. | 169.8 | 171.5 | 168.9 | 164.4 | 152.1 | 156.6 | 153.9 | 148.7 |

TABLE 65

Measurement of film thickness (μm)

| | Plasma treatment | | | | Mechanical energy treatment | | | | Untreated | | | |
|---|---|---|---|---|---|---|---|---|---|---|---|---|
| | Particle size | | | | | | | | | | | |
| Calcining temperature | 0.5 μm | 1 μm | 10 μm | 30 μm | 0.5 μm | 1 μm | 10 μm | 30 μm | 0.5 μm | 1 μm | 10 μm | 30 μm |
| 600° C. | 33.6 | 37.9 | 36.1 | 34.7 | 32.9 | 36.0 | 34.7 | 33.2 | 32.7 | 36.3 | 34.7 | 33.6 |
| 1000° C. | 126.5 | 138.1 | 136.2 | 131.6 | 114.3 | 123.9 | 121.7 | 118.3 | 114.4 | 124.2 | 121.5 | 118.0 |
| 1200° C. | 140.1 | 143.8 | 140.5 | 136.3 | 125.6 | 128.4 | 125.3 | 121.5 | 125.8 | 128.1 | 125.4 | 121.3 |
| 1350° C. | 139.7 | 143.2 | 139.8 | 135.5 | 125.5 | 127.3 | 124.8 | 120.1 | 125.4 | 127.4 | 124.6 | 120.2 |

TABLE 66

Measurement of elution amount (ppm) of Ca

| | Mechanical energy → plasma treatment (separate treatments) | | | | Mechanical energy + plasma treatment (simultaneous treatments) | | | |
|---|---|---|---|---|---|---|---|---|
| | Particle size | | | | | | | |
| Calcining temperature | 0.5 μm | 1 μm | 10 μm | 30 μm | 0.5 μm | 1 μm | 10 μm | 30 μm |
| 600° C. | 172 | 154 | 146 | 149 | 191 | 178 | 171 | 173 |
| 1000° C. | 74 | 67 | 65 | 67 | 113 | 108 | 102 | 106 |
| 1200° C. | 47 | 42 | 39 | 40 | 73 | 66 | 63 | 66 |
| 1350° C. | 50 | 45 | 44 | 44 | 76 | 72 | 70 | 72 |

TABLE 67

| | Measurement of elution amount (ppm) of Ca | | | | | | | | | | | |
|---|---|---|---|---|---|---|---|---|---|---|---|---|
| | Plasma treatment | | | | Mechanical energy treatment | | | | Untreated | | | |
| | | | | | Particle size | | | | | | | |
| Calcining temperature | 0.5 μm | 1 μm | 10 μm | 30 μm | 0.5 μm | 1 μm | 10 μm | 30 μm | 0.5 μm | 1 μm | 10 μm | 30 μm |
| 600° C. | 212 | 198 | 191 | 192 | 237 | 224 | 215 | 220 | 235 | 224 | 217 | 218 |
| 1000° C. | 126 | 120 | 115 | 118 | 144 | 141 | 132 | 135 | 143 | 139 | 133 | 136 |
| 1200° C. | 82 | 73 | 71 | 73 | 94 | 83 | 81 | 81 | 92 | 84 | 81 | 83 |
| 1350° C. | 85 | 79 | 79 | 78 | 95 | 90 | 92 | 88 | 96 | 91 | 90 | 89 |

TABLE 68

| | Measurement of Vickers hardness (Hv) | | | | | | | |
|---|---|---|---|---|---|---|---|---|
| | Mechanical energy → plasma treatment (separate treatments) | | | | Mechanical energy + plasma treatment (simultaneous treatments) | | | |
| | Particle size | | | | | | | |
| Calcining temperature | 0.5 μm | 1 μm | 10 μm | 30 μm | 0.5 μm | 1 μm | 10 μm | 30 μm |
| 600° C. | 422 | 425 | 430 | 427 | 406 | 408 | 411 | 409 |
| 1000° C. | 445 | 451 | 454 | 452 | 420 | 424 | 427 | 425 |
| 1200° C. | 479 | 483 | 487 | 485 | 455 | 459 | 462 | 460 |
| 1350° C. | 477 | 486 | 488 | 484 | 453 | 460 | 464 | 459 |

TABLE 69

| | Measurement of Vickers hardness (Hv) | | | | | | | | | | | |
|---|---|---|---|---|---|---|---|---|---|---|---|---|
| | Plasma treatment | | | | Mechanical energy treatment | | | | Untreated | | | |
| | | | | | Particle size | | | | | | | |
| Calcining temperature | 0.5 μm | 1 μm | 10 μm | 30 μm | 0.5 μm | 1 μm | 10 μm | 30 μm | 0.5 μm | 1 μm | 10 μm | 30 μm |
| 600° C. | 378 | 383 | 388 | 386 | 351 | 351 | 355 | 355 | 349 | 354 | 356 | 353 |
| 1000° C. | 391 | 398 | 401 | 397 | 358 | 364 | 369 | 364 | 357 | 365 | 366 | 364 |
| 1200° C. | 422 | 427 | 430 | 426 | 383 | 389 | 391 | 387 | 380 | 387 | 389 | 388 |
| 1350° C. | 419 | 430 | 434 | 429 | 376 | 390 | 390 | 389 | 378 | 389 | 390 | 389 |

8-2 Powders in which 5% by Mass of Zinc Oxide was Blended as Color Tone Adjuster Films were formed by using the powders obtained by providing the above-mentioned treatments of 1) and 3) to 6) to the powders obtained by blending 5% by mass of zinc oxide as a color tone adjuster in the film-forming powders that were calcined in an argon atmosphere, ground and classified with the counter air flow mill. Results of the film thicknesses are shown in [Table 70] and [Table 71]. Results of the elution amounts of Ca are shown in [Table 72] and [Table 73]. And results of Vickers hardness are shown in [Table 74] and [Table 75].

TABLE 70

| | Measurement of film thickness (μm) | | | | | | | |
|---|---|---|---|---|---|---|---|---|
| | Mechanical energy → plasma treatment (separate treatments) | | | | Mechanical energy + plasma treatment (simultaneous treatments) | | | |
| | Particle size | | | | | | | |
| Calcining temperature | 0.5 μm | 1 μm | 10 μm | 30 μm | 0.5 μm | 1 μm | 10 μm | 30 μm |
| 600° C. | 39.5 | 45.1 | 46.2 | 41.4 | 36.0 | 41.4 | 42.7 | 38.3 |
| 1000° C. | 146.9 | 161.4 | 164.1 | 153.8 | 135.2 | 149.3 | 152.6 | 143.7 |
| 1200° C. | 157.3 | 168.7 | 174.3 | 165.1 | 142.3 | 153.7 | 159.0 | 149.9 |
| 1350° C. | 157.0 | 168.2 | 173.6 | 163.3 | 141.9 | 153.1 | 158.4 | 148.5 |

TABLE 71

| | Measurement of film thickness (μm) | | | | | | | | | | | |
|---|---|---|---|---|---|---|---|---|---|---|---|---|
| | Plasma treatment | | | | Mechanical energy treatment | | | | Untreated | | | |
| | Particle size | | | | | | | | | | | |
| Calcining temperature | 0.5 μm | 1 μm | 10 μm | 30 μm | 0.5 μm | 1 μm | 10 μm | 30 μm | 0.5 μm | 1 μm | 10 μm | 30 μm |
| 600° C. | 32.5 | 37.2 | 38.3 | 34.3 | 31.5 | 36.0 | 36.4 | 32.8 | 31.6 | 35.8 | 36.8 | 33.1 |
| 1000° C. | 124.0 | 135.1 | 138.9 | 131.0 | 111.2 | 121.1 | 124.6 | 117.1 | 111.0 | 121.5 | 124.7 | 117.4 |
| 1200° C. | 130.3 | 140.8 | 145.4 | 137.2 | 116.6 | 124.5 | 129.3 | 122.0 | 116.3 | 124.8 | 129.0 | 121.9 |
| 1350° C. | 129.9 | 140.5 | 144.2 | 135.8 | 116.0 | 124.6 | 128.0 | 120.3 | 115.8 | 124.4 | 127.9 | 120.6 |

TABLE 72

| | Measurement of elution amount (ppm) of Ca | | | | | | | |
|---|---|---|---|---|---|---|---|---|
| | Mechanical energy → plasma treatment (separate treatments) | | | | Mechanical energy + plasma treatment (simultaneous treatments) | | | |
| | Particle size | | | | | | | |
| Calcining temperature | 0.5 μm | 1 μm | 10 μm | 30 μm | 0.5 μm | 1 μm | 10 μm | 30 μm |
| 600° C. | 169 | 147 | 149 | 152 | 189 | 169 | 174 | 179 |
| 1000° C. | 74 | 62 | 62 | 69 | 113 | 97 | 99 | 106 |
| 1200° C. | 50 | 36 | 43 | 47 | 69 | 55 | 67 | 72 |
| 1350° C. | 54 | 39 | 45 | 51 | 73 | 58 | 72 | 75 |

TABLE 73

| | Measurement of elution amount (ppm) of Ca | | | | | | | | | | | |
|---|---|---|---|---|---|---|---|---|---|---|---|---|
| | Plasma treatment | | | | Mechanical energy treatment | | | | Untreated | | | |
| | Particle size | | | | | | | | | | | |
| Calcining temperature | 0.5 μm | 1 μm | 10 μm | 30 μm | 0.5 μm | 1 μm | 10 μm | 30 μm | 0.5 μm | 1 μm | 10 μm | 30 μm |
| 600° C. | 207 | 187 | 189 | 199 | 235 | 214 | 215 | 221 | 231 | 211 | 215 | 222 |
| 1000° C. | 129 | 109 | 111 | 121 | 145 | 123 | 127 | 139 | 145 | 124 | 126 | 137 |
| 1200° C. | 77 | 62 | 75 | 81 | 86 | 73 | 87 | 93 | 87 | 71 | 86 | 92 |
| 1350° C. | 82 | 66 | 80 | 85 | 92 | 74 | 94 | 96 | 93 | 75 | 92 | 96 |

TABLE 74

Measurement of Vickers hardness (Hv)

| | Mechanical energy → plasma treatment (separate treatments) | | | | Mechanical energy + plasma treatment (simultaneous treatments) | | | |
|---|---|---|---|---|---|---|---|---|
| | Particle size | | | | | | | |
| Calcining temperature | 0.5 μm | 1 μm | 10 μm | 30 μm | 0.5 μm | 1 μm | 10 μm | 30 μm |
| 600° C. | 423 | 429 | 427 | 431 | 410 | 415 | 412 | 418 |
| 1000° C. | 442 | 447 | 446 | 452 | 429 | 437 | 434 | 436 |
| 1200° C. | 476 | 484 | 485 | 490 | 461 | 468 | 465 | 470 |
| 1350° C. | 480 | 489 | 488 | 487 | 462 | 469 | 463 | 468 |

TABLE 75

Measurement of Vickers hardness (Hv)

| | Plasma treatment | | | | Mechanical energy treatment | | | | Untreated | | | |
|---|---|---|---|---|---|---|---|---|---|---|---|---|
| | Particle size | | | | | | | | | | | |
| Calcining temperature | 0.5 μm | 1 μm | 10 μm | 30 μm | 0.5 μm | 1 μm | 10 μm | 30 μm | 0.5 μm | 1 μm | 10 μm | 30 μm |
| 600° C. | 380 | 387 | 386 | 392 | 348 | 357 | 353 | 360 | 351 | 357 | 354 | 359 |
| 1000° C. | 394 | 403 | 402 | 406 | 362 | 365 | 366 | 372 | 360 | 368 | 366 | 370 |
| 1200° C. | 427 | 434 | 431 | 433 | 383 | 388 | 391 | 393 | 383 | 389 | 388 | 392 |
| 1350° C. | 425 | 432 | 435 | 431 | 385 | 393 | 392 | 392 | 384 | 392 | 390 | 391 |

8-3 Powders in Which 0.1% by Mass of Red No. 204 Was Blended as Color Tone Adjuster Films were formed by using the powders obtained by providing the above-mentioned treatments of 1) and 3) to 6) to the powders obtained by blending 0.1% by mass of Red No. 204 as a color tone adjuster in the film-forming powders that were calcined in an argon atmosphere, ground and classified with the counter air flow mill. Results of the film thicknesses are shown in [Table 76] and [Table 77]. Results of the elution amounts of Ca are shown in [Table 78] and [Table 79]. And results of Vickers hardness are shown in [Table 80] and [Table 81].

TABLE 76

Measurement of film thickness (μm)

| Calcining temperature | Mechanical energy → plasma treatment (separate treatments) 1 μm | Mechanical energy + plasma treatment (simultaneous treatments) 1 μm |
|---|---|---|
| 600° C. | 43.7 | 40.3 |
| 1000° C. | 157.2 | 144.7 |
| 1200° C. | 165.6 | 150.3 |
| 1350° C. | 165.1 | 149.8 |

TABLE 77

Measurement of film thickness (μm)

| Calcining temperature | Plasma treatment 1 μm | Mechanical energy treatment 1 μm | Untreated 1 μm |
|---|---|---|---|
| 600° C. | 36.5 | 35.2 | 35.1 |
| 1000° C. | 130.9 | 118.5 | 118.6 |
| 1200° C. | 136.7 | 123.1 | 122.8 |
| 1350° C. | 136.6 | 122.5 | 122.5 |

TABLE 78

Measurement of elution amount (ppm) of Ca

| Calcining temperature | Mechanical energy → plasma treatment (separate treatments) 1 μm | Mechanical energy + plasma treatment (simultaneous treatments) 1 μm |
|---|---|---|
| 600° C. | 153 | 171 |
| 1000° C. | 66 | 102 |
| 1200° C. | 39 | 59 |
| 1350° C. | 41 | 60 |

TABLE 79

Measurement of elution amount (ppm) of Ca

| Calcining temperature | Plasma treatment 1 μm | Mechanical energy treatment 1 μm | Untreated 1 μm |
|---|---|---|---|
| 600° C. | 189 | 210 | 210 |
| 1000° C. | 112 | 129 | 126 |
| 1200° C. | 66 | 75 | 75 |
| 1350° C. | 67 | 76 | 77 |

TABLE 80

Measurement of Vickers hardness (Hv)

| Calcining temperature | Mechanical energy → plasma treatment (separate treatments) Particle size 1 μm | Mechanical energy + plasma treatment (simultaneous treatments) Particle size 1 μm |
| --- | --- | --- |
| 600° C. | 426 | 413 |
| 1000° C. | 453 | 432 |
| 1200° C. | 482 | 466 |
| 1350° C. | 480 | 465 |

TABLE 81

Measurement of Vickers hardness (Hv)

| Calcining temperature | Plasma treatment Particle size 1 μm | Mechanical energy treatment Particle size 1 μm | Untreated Particle size 1 μm |
| --- | --- | --- | --- |
| 600° C. | 384 | 355 | 356 |
| 1000° C. | 402 | 371 | 369 |
| 1200° C. | 429 | 385 | 388 |
| 1350° C. | 427 | 386 | 387 |

[Characteristics of Film-Forming Powder]

In order to examine the difference in the properties of film-forming hydroxyapatite powders provided with respective treatments, the characteristics of the film-forming powders were investigated by X-ray powder diffraction tests and laser Raman spectroscopy tests.

9-1 X-Ray Powder Diffraction Tests

The X-ray powder diffraction tests were conducted under the following conditions: target: Cu, tube voltage: 45 kV, tube current: 40 mA, and scanning zone: 2θ=5 to 60° by using an X-ray powder diffractometer (Empyrean, manufactured by PANalytical Japan) on the three samples of the hydroxyapatite powder (HAP) having a mean particle size of 1 μm that was produced in Example 2-1 (only calcined, ground, classified and mixed, and provided with no treatment of plasma irradiation and/or application of mechanical energy); the film-forming powder having a mean particle size of 1 μm that was produced in Example 7-2 and obtained by providing this hydroxyapatite powder with the treatments of application of mechanical energy followed by plasma irradiation; and the film-forming powder having a mean particle size of 1 μm obtained by providing the treatments of application of mechanical energy followed by plasma irradiation to the film-forming hydroxyapatite powder obtained in Example 8-1 blended with 1% by mass of titanium oxide. Results are shown in FIG. 4. Consequently, all diffraction patterns were the same, and no difference among the powders in these samples could be found.

9-2 Laser Raman Spectroscopy Tests

Since the crystallinity change in the near surfaces of powder particles could not be confirmed by the X-ray powder diffraction tests, examination by a Raman spectroscopy was performed. The characteristics were investigated by using a laser Raman spectrometer (InVia Reflex, manufactured by Renishaw plc.) for the five samples of the powders having a mean particle size of 1 μm that were produced in Example 7-2 and that were provided with the following respective treatments: 1) the treatment of application of mechanical energy followed by plasma irradiation (mechanical energy→plasma treatment, separate treatments); 3) the treatment of application of mechanical energy and plasma irradiation simultaneously (mechanical energy=plasma treatment, simultaneous treatments); 4) the treatment of plasma irradiation (plasma treatment); 5) the treatment of application of mechanical energy (mechanical energy treatment), and the powder having a mean particle size of 1 μm that was produced in Example 7-2 and that was 6) only calcined, ground, classified, mixed and provided with no treatment of plasma irradiation and/or application of mechanical energy (untreated).

Changes in the peak intensity of the above-mentioned one untreated sample to the peak intensities of the above-mentioned four treated samples were compared as to peaks near 960 cm$^{-1}$ attributed to hydroxyapatite. Changes in the peak intensities of laser Raman spectra are shown in [Table 82] and FIG. 5. Consequently, it was found that when plasma treatment was performed, the peak intensities became higher than the intensity of untreated samples. It was also found that when the treatment of performing mechanical energy treatment and plasma treatment simultaneously was provided, the peak intensity near 960 cm$^{-1}$ became higher and when plasma treatment was performed successively after mechanical energy treatment was performed, the peak intensity near 960 cm$^{-1}$ became still higher. This shows that the crystallinity on the surfaces of particles was improved, and proves that the composite formation of particles accompanied with high crystallization due to a mechanochemical effect by mechanical energy and plasma treatment occurred.

TABLE 82

| | Peak intensity | Rate of increase (%) |
| --- | --- | --- |
| Untreated (before treatment) | 518.5 | — |
| Mechanical energy treatment | 756.5 | 146 |
| Plasma treatment | 1634.7 | 315 |
| Mechanical energy + plasma treatment (simultaneous treatments) | 2321.5 | 448 |
| Mechanical energy → plasma treatment (separate treatments) | 3834.0 | 739 |

Example 10

[Multilayer of Formed Film Layer]

A film of a tooth crown color tone adjusting material (white color, 1% of titanium oxide blended) was formed on a glass plate. On this first layer, a film of a tooth crown color tone adjusting material (a color similar to a tooth color, 5% of zinc oxide blended) was formed as the second layer. On this second layer, a film of a tooth crown color tone adjusting material (a transparent color (as a topcoat), only hydroxyapatite) was formed as the third layer. The film formation conditions of the first layer, the second layer and the third layer were all the same. The conditions were set as follows: the inner diameter of a handpiece tip nozzle: 1.8 mm and the spray pressure: 0.5 MPa. Films were formed under conditions of a distance between a spray nozzle tip and a substrate of 1.0 mm (with the nozzle tip supported perpendicularly to a substrate) and a moving speed of the spray nozzle of 5 mm/s. A result (photograph) is shown in FIG. 7. The cross section image of the multilayer of formed film layers shown in FIG. 7 by a laser microscope is shown in FIG. 8.

The photographs of the formed film layers formed in parts on the surfaces of teeth by using the film-forming powders in which the color tone adjusters were blended of Example 2-3 ((1% of titanium oxide blended, left figure), (5% of zinc oxide blended, right figure)) under the following film formation conditions: the inner diameter of a handpiece tip nozzle: 1.8 mm, the spray pressure: 0.5 MPa, the distance between a spray nozzle tip and a substrate: 1.0 mm (with the nozzle tip supported perpendicularly to a substrate), and the moving speed of the spray nozzle: 5 mm/s are shown as FIG. 9.

INDUSTRIAL APPLICABILITY

The film-forming powders of the present invention are useful in the field of dental treatment.

EXPLANATION OF LETTERS OR NUMERALS

1: AC/DC converter of plasma generator,
2: cold-cathode tube inverter of plasma generator,
3: booster circuit of plasma generator (Cockcroft-Walton circuit),
4: plasma nozzle of plasma generator,
5: gas flowmeter of plasma generator.

The invention claimed is:

1. A film-forming powder for forming a film on a surface of a tooth for use in a jet-device for a tooth, the powder having a mean particle size of 0.5 to 30 μm, wherein the film-forming powder is produced by calcining an apatite represented by $Ca_{10-X} \cdot M_X(ZO_4)_6Y_2$ (wherein X represents 0 to 10; M represents a metal or hydrogen; $ZO_4$ represents $PO_4$, $CO_3$, $CrO_4$, $AsO_4$, $VO_4$, $SiO_4$, $SO_4$ or $GeO_4$; and Y represents a hydroxyl group, a halogen element or a carbonate group) in an atmosphere consisting of an argon gas or a nitrogen gas at 600 to 1350° C.

2. The film-forming powder according to claim 1, wherein the apatite is hydroxyapatite.

3. The film-forming powder according to claim 1, wherein a color tone adjuster for adjusting a color tone of a tooth crown is further blended in the film-forming powder.

4. The film-forming powder according to claim 3, wherein the color tone adjuster of a tooth crown is at least one selected from titanium oxide, zinc oxide, and ultramarine blue and a red pigment.

5. The film-forming powder according to claim 1, wherein the film-forming powder is produced by plasma irradiation.

6. The film-forming powder according to claim 5, wherein the film-forming powder is produced by further applying mechanical energy.

7. The film-forming powder according to claim 6, wherein the film-forming powder is produced by application of mechanical energy followed by plasma irradiation.

8. The film-forming powder according to claim 5, wherein the plasma irradiation is plasma irradiation in which helium gas is used as an irradiation gas.

9. The film-forming powder according to claim 1, wherein a film thickness of a formed film is 30 μm or more, and Vickers hardness is 340 Hv or more when the powder is sprayed on a substrate under conditions of an inner diameter of a handpiece tip nozzle of 0.5 to 5.0 mm, a spray pressure of 0.2 to 0.8 MPa, a distance between a spray nozzle tip and the substrate of 0.1 to 3.0 cm, and a moving speed of the spray nozzle of 0 to 10 mm/s.

10. A method for producing a film-forming powder for forming a film on a surface of a tooth for use in a jet-device for a tooth, the powder having a mean particle size of 0.5 to 30 μm, comprising calcining an apatite represented by $Ca_{10-X} \cdot M_X(ZO_4)_6Y_2$ (wherein X represents 0 to 10; M represents a metal or hydrogen; $ZO_4$ represents $PO_4$, $CO_3$, $CrO_4$, $AsO_4$, $VO_4$, $SiO_4$, $SO_4$ or $GeO_4$; and Y represents a hydroxyl group, a halogen element or a carbonate group) in an atmosphere consisting of an argon gas or a nitrogen gas at 600 to 1350° C., and then performing grinding and classification.

11. The method for producing a film-forming powder according to claim 10, wherein the apatite is hydroxyapatite.

12. The method for producing a film-forming powder according to claim 10, comprising further blending a color tone adjuster for adjusting a color tone of a tooth crown.

13. The method for producing a film-forming powder according to claim 12, wherein the color tone adjuster of a tooth crown is at least one selected from titanium oxide, zinc oxide, ultramarine blue and a red pigment.

14. The method for producing a film-forming powder according to claim 10, comprising further performing plasma irradiation after grinding and classification.

15. The method for producing a film-forming powder according to claim 14, comprising further applying mechanical energy.

16. The method for producing a film-forming powder according to claim 15, wherein plasma irradiation is performed after applying mechanical energy.

17. The method for producing a film-forming powder according to claim 14, wherein the plasma irradiation is plasma irradiation in which helium gas is used as an irradiation gas.

18. The method for producing a film-forming powder according to claim 10, wherein a film thickness of a formed film is 30 μm or more, and Vickers hardness is 340 Hv or more when the powder is sprayed on a substrate under conditions of an inner diameter of a handpiece tip nozzle of 0.5 to 5.0 mm, a spray pressure of 0.2 to 0.8 MPa, a distance between a spray nozzle tip and a substrate of 0.1 to 3.0 cm, and a moving speed of the spray nozzle of 0 to 10 mm/s.

19. A pellet comprising the film-forming powder according to claim 1.

* * * * *